United States Patent
Lee et al.

(10) Patent No.: US 9,127,309 B2
(45) Date of Patent: Sep. 8, 2015

(54) METHODS OF NUCLEIC ACID QUANTIFICATION AND DETECTION USING ANOMALOUS MIGRATION

(75) Inventors: Ming-Chou Lee, San Juan Capistrano, CA (US); Sergey V. Voronov, Sharon, MA (US); Laurence R. McCarthy, Great Falls, VA (US); Lilly I. Kong, Covina, CA (US); Vesselin Tenkov Diankov, Franklin, MA (US)

(73) Assignee: Qiagen Mansfield, Inc., Mansfield, MA (US)

( * ) Notice: Subject to any disclaimer, the term of this patent is extended or adjusted under 35 U.S.C. 154(b) by 121 days.

(21) Appl. No.: 13/982,299

(22) PCT Filed: Jan. 31, 2012

(86) PCT No.: PCT/US2012/023234
§ 371 (c)(1),
(2), (4) Date: Mar. 11, 2014

(87) PCT Pub. No.: WO2012/106288
PCT Pub. Date: Aug. 9, 2012

(65) Prior Publication Data
US 2014/0178872 A1    Jun. 26, 2014

Related U.S. Application Data

(60) Provisional application No. 61/438,093, filed on Jan. 31, 2011.

(51) Int. Cl.
*C12Q 1/68* (2006.01)

(52) U.S. Cl.
CPC ............ *C12Q 1/6816* (2013.01); *C12Q 1/6851* (2013.01)

(58) Field of Classification Search
None
See application file for complete search history.

(56) References Cited

U.S. PATENT DOCUMENTS

| | | |
|---|---|---|
| 5,210,015 A | 5/1993 | Gelfand et al. |
| 5,538,848 A | 7/1996 | Livak et al. |
| 2008/0102444 A1 | 5/2008 | Lee et al. |
| 2009/0197254 A1 | 8/2009 | Lee et al. |

FOREIGN PATENT DOCUMENTS

WO    2010/067055    6/2010

*Primary Examiner* — James Martinell
(74) *Attorney, Agent, or Firm* — Nixon Peabody LLP; Mark J. FitzGerald

(57) ABSTRACT

Described are approaches for the identification, detection, and quantification of nucleic acids in a biological sample. These methods are based, in part, on the elucidation of anomalous migration properties of short nucleic acid molecules when conjugated to a fluorescent label, such as fluorescein labels, such that a smaller nucleic acid reliably migrates slower than a larger nucleic acid under the same conditions of separation.

23 Claims, 13 Drawing Sheets

C

D

E

F

METHODS OF NUCLEIC ACID QUANTIFICATION AND DETECTION USING ANOMALOUS MIGRATION

CROSS-REFERENCE TO RELATED APPLICATIONS

This application is a 35 U.S.C. §371 National Phase Entry Application of International Application No. PCT/US2012/023234 filed Jan. 31, 2012, which designates the U.S., and which claims benefit under 35 U.S.C. §119(e) of U.S. Provisional Patent Application Ser. No. 61/438,093 filed Jan. 31, 2011, the contents of which are incorporated herein by reference in their entireties.

FIELD OF THE INVENTION

This invention generally relates to the field of nucleic acid chemistry, specifically methods for detection and quantification of nucleic acids.

BACKGROUND

Since the advent of the polymerase chain reaction (PCR) it has been recognized that nucleic acid amplification methodologies can be used to estimate the initial concentration of a template nucleic acid, providing what is known as quantitative PCR. However, variations in the efficiency or other aspects of an amplification can and do result from a number of different influences on the reactions. Multiplex quantitative PCR, while providing benefits in determining concentrations of multiple nucleic acid sequences in a mixture, presents additional challenges, such as the need for multiple, unique probe sets having different detectable labels.

SUMMARY OF INVENTION

Described herein are approaches for the identification, detection, and quantification of nucleic acids in a biological sample. These approaches are based, in part, on the elucidation of anomalous migration properties of short nucleic acid molecules when conjugated to a fluorescent label, such as fluorescein labels, such that a smaller nucleic acid reliably migrates slower than a larger nucleic acid under the same conditions of separation. The anomalous migration pattern is exploited in the methods described herein to identify and quantify target nucleic acids in a sample by detecting and quantifying a product, e.g., labeled detection molecule, that is generated due to a 5' to 3' nuclease activity of a nucleic acid polymerase on a detectably labeled oligonucleotide probe hybridized to a target nucleic acid. The approaches described herein are useful in the specific detection and quantification of an individual target nucleic acid in a sample, but also provide multiplex formats and approaches for the detection and quantification of multiple target nucleic acids in a sample, using, for example, multiple detectably labeled oligonucleotide probes having different sizes and/or labels.

Accordingly, in one aspect, provided herein, is a method for the detection of a target nucleic acid in a sample, the method comprising the steps of:
a) providing a nucleic acid sample comprising an oligonucleotide primer and a labeled oligonucleotide probe member hybridized to a target nucleic acid, wherein the primer and probe member are hybridized to the same strand of the same target nucleic acid molecule in the sample, where i) the primer hybridizes 5' of the probe member on the target nucleic acid; ii) the probe member hybridizes with the target at the probe's 3' end and comprises a 5' overhang sequence of 0 to n nucleotides that do not hybridize to the target nucleic acid; and iii) where the label on the labeled probe is attached to the 5' terminal nucleotide of the probe when 5' overhang=0, or to one of the n non-hybridizing nucleotides when n>0;
b) maintaining the sample of step (a) with a template-dependent nucleic acid polymerase having 5' to 3' nuclease activity, under conditions sufficient to permit the 5' to 3' nuclease activity of the polymerase to cleave hybridized probe member to release a labeled detection molecule;
c) separating nucleic acids in the sample by electrophoresis; and
d) detecting the labeled detection molecule in the separated nucleic acids, where the labeled detection molecule indicates the presence of the target molecule, and where the FAM-labeled detection molecule is detected in an anomalous migration position for non-hybridizing overhangs of n=0 to 6, with n=1 migrating faster than n=0, n=2 migrating faster than n=1, n=3 migrating faster than n=2, n=4 migrating faster than n=3, n=5 migrating faster than n=4, and n=6 migrating faster than n=5, and where the FAM-labeled detection molecules released from probes with non-hybridizing overhangs greater than n=6 show little change in migration where n is close to 6, and thereafter migrating progressively slower with increasing overhang length.

Provided herein, in one aspect, is a method for the detection of a target nucleic acid in a sample, the method comprising the steps of:
a) contacting a nucleic acid sample under hybridizing conditions with an oligonucleotide primer and a labeled oligonucleotide probe member to create a mixture of hybridized duplexes comprising a primer and a probe member hybridized to the same strand of the same target nucleic acid molecule in the sample, where i) the primer hybridizes 5' of the probe member on the target nucleic acid; ii) the probe member hybridizes with the target at the probe's 3' end and comprises a 5' overhang sequence of 0 to n nucleotides that do not hybridize to the target nucleic acid; and iii) where the label on the labeled probe is attached to the 5' terminal nucleotide of the probe when 5' overhang=0, or to one of the n non-hybridizing nucleotides when n>0;
b) maintaining the mixture of step (a) with a template-dependent nucleic acid polymerase having 5' to 3' nuclease activity, under conditions sufficient to permit the 5' to 3' nuclease activity of the polymerase to cleave hybridized probe member to release a labeled detection molecule;
c) separating nucleic acids in the mixture by electrophoresis; and
d) detecting the labeled detection molecule in the separated nucleic acids, where the labeled detection molecule indicates the presence of the target molecule, and where the FAM-labeled detection molecule is detected in an anomalous migration position for non-hybridizing overhangs of n=0 to 6, with n=1 migrating faster than n=0, n=2 migrating faster than n=1, n=3 migrating faster than n=2, n=4 migrating faster than n=3, n=5 migrating faster than n=4, and n=6 migrating faster than n=5, and where the FAM-labeled detection molecules released from probes with non-hybridizing overhangs greater than n=6 show little change in migration where n is close to 6, and thereafter migrating progressively slower with increasing overhang length.

In one embodiment of this and other aspects described herein, the oligonucleotide probe is labeled with FAM.

In some embodiments of this aspect, the method permits the detection of a plurality of target nucleic acids in the same nucleic acid sample, such that step (a) comprises contacting the nucleic acid sample with a primer and probe mixture comprising a different oligonucleotide primer and labeled oligonucleotide probe member for each of the plurality of target nucleic acids, where each of the different labeled oligonucleotide probe members comprises a different length of non-hybridizing overhang, and where the detection of a plurality of the anomalously migrating detection molecules in step (d) indicates the presence of a plurality of the target molecules. In some such embodiments, the labeled probe members comprise non-hybridizing 5' overhangs of 0 to 6 nucleotides.

In some embodiments of this aspect, when n=0, i.e., when there is no overhang, FAM-labeled detection molecule has an apparent migration approximately corresponding to that of a 95 base polynucleotide labeled with FAM.

In some embodiments of this aspect, the method permits the detection of a plurality of target nucleic acids in the same nucleic acid sample, such that step (a) comprises contacting the nucleic acid sample with a different oligonucleotide primer and detectably labeled oligonucleotide probe member for each of the plurality of target nucleic acids, where respective ones of one or more of the detectably labeled oligonucleotide probe members comprise different detectable labels, and where the detection of labeled detection molecules comprising the different detectable labels indicates the presence of a plurality of the target molecules. In some such embodiments, the detectable labels comprise different fluorescent labels.

In those embodiments where the method permits the detection of a plurality of target nucleic acids in the same nucleic acid sample, step (a) can comprise contacting the nucleic acid sample with a different oligonucleotide primer and detectably labeled oligonucleotide probe member for each of the plurality of target nucleic acids, where respective ones of one or more of the detectably labeled oligonucleotide probe members comprise different detectable labels. In some such embodiments, the detectable labels comprise different fluorescent labels.

In some embodiments of these methods, the 3' end of the oligonucleotide primer hybridizes within about 20 nucleotides of the 5' end of the labeled oligonucleotide probe member, thereby having spacing effective to permit the release of labeled fragments in the absence of nucleic acid polymerization.

In some embodiments of these methods, the nucleic acid polymerase is a DNA polymerase having a 5' to 3' nuclease activity. In some such embodiments, the DNA polymerase is selected from the group consisting of Taq polymerase and variants thereof having 5' to 3' exonuclease activity, and commercial products based on Taq polymerase that retain 5' to 3' exonuclease activity (e.g., HotStart Taq™ (Qiagen), AptaTaq™ (Roche), and AmpliTaq Gold™ (Applied Biosystems); *Thermus thermophilus* (Tth) DNA polymerase; *Bacillus stearothermophilus* DNA polymerase; *Thermus flavus* (Tfl) polymerase; *Thermus brocianus* polymerase; and *E. coli* DNA polymerase.

In some embodiments of these methods, the nucleic acid polymerase is a thermostable polymerase. In some embodiments of these methods, the nucleic acid polymerase is a thermostable polymerase and step (b) comprises a plurality of cycles of: i) maintaining the mixture of step (a) at a temperature that permits annealing of the primer and probe; ii) maintaining the mixture of step (a) at a temperature and under conditions that permit polymerization by said polymerase; and iii) maintaining the mixture at a temperature and for a time sufficient to separate the strands of nucleic acids in said mixture.

In some embodiments of these methods, the 3' terminal nucleotide of the labeled oligonucleotide probe cannot be extended by the polymerase.

Also provided herein, in another aspect, is a method for the detection of a target nucleic acid in a sample, the method comprising the steps of:

a) contacting a nucleic acid sample under hybridizing conditions with a pair of oligonucleotide primers and a labeled oligonucleotide probe to create a mixture of hybridized duplexes of the pair of oligonucleotide primers and the labeled probe annealed to a target nucleic acid present in the sample, where the pair of oligonucleotide primers comprises a first oligonucleotide primer that hybridizes to the antisense of a 5' region of the target nucleic acid and a second oligonucleotide primer that hybridizes to a 3' region of the target nucleic acid, where the first oligonucleotide primer and the labeled oligonucleotide probe hybridize to the same strand of the target nucleic acid, wherein the 5' and 3' regions of the target sequence flank a region of the target sequence to which the labeled oligonucleotide probe hybridizes, and where the labeled oligonucleotide probe comprises a 5' overhang sequence of 0 to n nucleotides that does not hybridize to the target nucleic acid, and wherein the label on the probe is attached to the 5' terminal nucleotide of the probe when the 5' overhang=0 or to one of the n non-hybridizing nucleotides when n>0;

b) PCR amplifying target nucleic acid molecules present in the sample by a plurality of cycles of: i) extending annealed oligonucleotide primers using a thermostable nucleic acid polymerase having 5' to 3' exonuclease activity, under conditions sufficient to permit primer extension of annealed oligonucleotide primers and to permit the 5' to 3' nuclease activity to cleave annealed oligonucleotide probe to thereby release a labeled detection molecule; ii) heating to separate nucleic acid strands generated in step (i); and iii) maintaining under temperature conditions that permit annealing of oligonucleotide primer pairs and labeled oligonucleotide probes to target nucleic acids present in said sample;

c) separating nucleic acids generated in step (b); and d) detecting a released labeled detection molecule in the separated nucleic acids to thereby detect the presence and/or amount of the target nucleic acid present in the sample, where the labeled detection molecule is detected in an anomalous migration position for a non-hybridizing overhang of n=0 to 6, with n=1 migrating faster than n=0, n=2 migrating faster than n=1, n=3 migrating faster than n=2, n=4 migrating faster than n=3, n=5 migrating faster than n=4, and n=6 migrating faster than n=5, and where the labeled detection molecules released from probes with non-hybridizing overhangs greater than n=6 show little change in migration with increasing overhang length, until migration migrate progressively slower with increasing overhang length.

In some embodiments of this aspect, the separating comprises capillary electrophoresis.

In some embodiments of this aspect, the detectably labeled probe member comprises a non-hybridizing 5' overhang of 0 to 6 nucleotides.

In some embodiments of this aspect, when n=0, i.e., when there is no overhang, FAM-labeled detection molecule has an apparent migration approximately corresponding to that of a 95 base polynucleotide labeled with FAM.

In some embodiments of this aspect, the 3' terminal nucleotide of the labeled oligonucleotide probe cannot be extended by the polymerase.

Another aspect provides a method for the multiplex detection of target nucleic acids in a sample, the method comprising:

a) contacting a nucleic acid sample under hybridizing conditions with a pair of oligonucleotide primers and a fluorescently labeled oligonucleotide probe for each member of a plurality of different nucleic acid targets to be detected in the sample, to create a mixture of hybridized duplexes of the pair of oligonucleotide primers and the fluorescently labeled probe specific for each target nucleic acid member present in the sample, where: i) the pair of oligonucleotide primers for each nucleic acid target comprises a first oligonucleotide primer that hybridizes to the antisense of a 5' region of the target nucleic acid and a second oligonucleotide primer that hybridizes to a 3' region of the target nucleic acid; ii) the 5' and 3' regions of the target sequence flank a region of the target sequence which is complementary to the fluorescently labeled oligonucleotide probe for each nucleic acid target; iii) the first oligonucleotide primer and the fluorescently labeled oligonucleotide probe for each nucleic acid target hybridize to the same strand of the target nucleic acid; and iv) at least one fluorescently labeled probe is FAM-labeled, and wherein when the fluorescently labeled probe is FAM-labeled, said probe comprises a 5' overhang sequence of 0 to n nucleotides that do not hybridize to the target nucleic acid, where the FAM label on the labeled probe is attached to the 5' terminal nucleotide of the probe when the overhang=0 or to one of the n non-hybridizing nucleotides when n>0, and v) the length n of 5' overhang sequence and/or the identity of the label differs for each different target sequence to be detected, and wherein each different FAM-labeled probe molecule has a different length of 5' overhang;
b) PCR amplifying target nucleic acid molecules present in the sample by a plurality of cycles of: i) extending annealed oligonucleotide primers using a nucleic acid polymerase having 5' to 3' exonuclease activity, under conditions sufficient to permit primer extension of annealed oligonucleotide primers and to permit the 5' to 3' nuclease activity to cleave annealed oligonucleotide probes and thereby release a labeled detection molecule specific for each of the plurality of target nucleic acids present in said sample; ii) heating to separate nucleic acid strands generated in step (i); and iii) annealing oligonucleotide primer pairs and labeled oligonucleotide probes to target nucleic acids present in the sample;
c) separating nucleic acids generated in step (b) such that detection molecules specific for each of the target nucleic acids present in the sample can be identified; and
d) detecting each of the detection molecules released, whereby the presence and/or amount of each of the plurality of target nucleic acids present in the sample is indicated, where FAM-labeled detection molecules are detected in an anomalous migration position for a non-hybridizing overhang of n=0 to 6, with n=1 migrating faster than n=0, n=2 migrating faster than n=1, n=3 migrating faster than n=2, n=4 migrating faster than n=3, n=5 migrating faster than n=4, and n=6 migrating faster than n=5, and where the FAM-labeled detection molecules released from probes with non-hybridizing overhangs greater than n=6 show little change in migration where n is close to 6, and thereafter migrating progressively slower with increasing overhang length.

In some embodiments of this aspect, respective ones of the labeled oligonucleotide probes comprise different distinguishable fluorescent labels.

In some embodiments of this aspect, the separating comprises capillary electrophoresis.

In some embodiments of this aspect, where n=0, the FAM-labeled detection molecule has an apparent migration corresponding to that of a 95 base polynucleotide labeled with FAM.

In some embodiments of this aspect, the 3' terminal nucleotide of each of the labeled oligonucleotide probes cannot be extended by said polymerase.

In some embodiments of this aspect, where each of the labeled detection molecules specific for each of the target molecules present in the sample differs from each other in one or both of a) the type or identity of label on the released detection molecule and b) the separation characteristics of the released detection molecule. In some such embodiments, the separation characteristics comprise mass, length, charge, or a combination thereof.

Definitions

As used herein, the terms "sample" or, more particularly, "nucleic acid sample" refer to any substance containing or presumed to contain a nucleic acid, and includes, for example, a cellular extract, or a tissue extract or fluid extract isolated from an individual(s) or organism, or any polynucleotide(s) purified or isolated from such cellular, tissue or fluid extracts, including, but not limited to, skin, plasma, serum, spinal fluid, lymph fluid, synovial fluid, urine, tears, blood cells, organs, tumors, and also to samples of in vitro cell culture constituents (including, but not limited to, conditioned medium resulting from the growth of cells (including prokaryotic and eukaroyotic cells) in cell culture medium, recombinant cells, and cell components). Nucleic acid samples from environmental sources are also included.

As used herein, the terms "nucleic acid," "polynucleotide," and "oligonucleotide" generally refer to any polyribonucleotide or poly-deoxyribonucleotide, and includes unmodified RNA, unmodified DNA, modified RNA, and modified DNA. Polynucleotides include, without limitation, single- and double-stranded DNA and RNA polynucleotides. The term polynucleotide, as it is used herein, embraces chemically, enzymatically or metabolically modified forms of polynucleotides, as well as the naturally occurring chemical forms of DNA and RNA found in or characteristic of viruses and cells, including for example, simple (prokaryotic) and complex (eukaryotic) cells. A polynucleotide useful for the methods described herein can be an isolated or purified polynucleotide; it can be an amplified polynucleotide in an amplification reaction, or a transcribed product from an in vitro transcription reaction.

Accordingly, as used herein, the terms nucleic acid, polynucleotide and oligonucleotide also encompass primers and probes, as well as oligonucleotide fragments, and is generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases (including, but not limited to, abasic sites). There is no intended distinction in length between the term "nucleic acid," "polynucleotide," and "oligonucleotide," and these terms are used interchangeably. These terms refer only to the primary structure of the molecule. An oligonucleotide is not necessarily physically derived from any existing or natural sequence but can be generated in any manner, including chemical synthesis, DNA replication, reverse transcription or a combination thereof.

The terms "nucleotide" or "mononucleotide," as used herein, refer to a phosphate ester of a nucleoside, e.g., mono-, di-, tri-, and tetraphosphate esters, wherein the most common site of esterification is the hydroxyl group attached to the C-5 position of the pentose (or equivalent position of a non-pentose "sugar moiety"). The term "nucleotide" includes both a conventional nucleotide and a non-conventional nucleotide which includes, but is not limited to, phosphorothioate, phosphite, ring atom modified derivatives, and the like.

As used herein, the term "conventional nucleotide" refers to one of the "naturally occurring" deoxynucleotides (dNTPs), including dATP, dTTP (or TTP), dCTP, dGTP, dUTP, and dITP.

As used herein, the term "nonextendable nucleotide" refers to nucleotides that prevent extention of a polynucleotide chain by a polymerase. Examples of such nucleotides include dideoxy nucleotides (ddA, ddT, ddG, ddC) that lack a 3'-hydroxyl on the ribose ring, thereby preventing 3' extension by DNA polymerases. Other examples of such nucleotides include, but are not limited to, inverted bases, which can be incorporated at the 3'-end of an oligo, leading to a 3'-3' linkage, which inhibits extension by DNA polymerases.

As used herein, the term "non-conventional nucleotide" refers to a nucleotide that is not a naturally occurring nucleotide. The term "naturally occurring" refers to a nucleotide that exists in nature without human intervention. In contradistinction, the term "non-conventional nucleotide" refers to a nucleotide that exists only with human intervention, i.e., an "artificial nucleotide." A "non-conventional nucleotide" can include a nucleotide in which the pentose sugar and/or one or more of the phosphate esters is replaced with a respective analog. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., including any associated counterions, if present. A non-conventional nucleotide can show a preference of base pairing with another non-conventional or "artificial" nucleotide over a conventional nucleotide (e.g., as described in Ohtsuki et al. 2001, Proc. Natl. Acad. Sci., 98: 4922-4925, hereby incorporated by reference). The base pairing ability may be measured by the T7 transcription assay as described in Ohtsuki et al. (supra). Other non-limiting examples of "non-conventional" or "artificial" nucleotides can be found in Lutz et al. (1998) Bioorg. Med. Chem. Lett., 8: 1149-1152); Voegel and Benner (1996) Helv. Chim. Acta 76, 1863-1880; Horlacher et al. (1995) Proc. Natl. Acad. Sci., 92: 6329-6333; Switzer et al. (1993), Biochemistry 32:10489-10496; Tor and Dervan (1993) J. Am. Chem. Soc. 115: 4461-4467; Piccirilli et al. (1991) Biochemistry 30: 10350-10356; Switzer et al. (1989) J. Am. Chem. Soc. 111: 8322-8323, all of which are hereby incorporated by reference. A "non-conventional nucleotide" can also be a degenerate nucleotide or an intrinsically fluorescent nucleotide.

Because mononucleotides are reacted to make poly- and oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring, and as the "3' end" if its 3' oxygen is not linked to a 5' phosphate of a subsequent mononucleotide pentose ring. As used herein, a nucleic acid sequence, even if internal to a larger oligonucleotide, also can be said to have 5' and 3' ends.

As used herein, "complementary" refers to the ability of a single strand of a polynucleotide (or portion thereof) to hybridize to an anti-parallel polynucleotide strand (or portion thereof) by contiguous base-pairing, i.e., hydrogen bonding, between the nucleotides of the anti-parallel polynucleotide single strands, thereby forming a double-stranded polynucleotide comprising the complementary strands. A first polynucleotide is said to be "completely complementary" to a second polynucleotide strand if each and every nucleotide of the first polynucleotide forms a hydrogen-bonded base-pair with nucleotides within the complementary region of the second polynucleotide. A first polynucleotide is not completely complementary (i.e., "partially complementary") to the second polynucleotide if at least one nucleotide in the first polynucleotide does not base pair with the corresponding nucleotide in the second polynucleotide. The degree of complementarity between polynucleotide strands has significant effects on the efficiency and strength of annealing or hybridization between polynucleotide strands. This is of particular importance in amplification reactions, such as those described herein, which depend upon binding between polynucleotide strands. Accordingly, an oligonucleotide primer or oligonucleotide probe is "complementary" to a strand of a target nucleic acid if at least 50% (preferably, at least 60%, more preferably at least 70%, at least 80%, still more preferably at least 90% or more, up to and including 100%) of the nucleotides of the primer or probe form base-pairs with nucleotides on the target polynucleotide.

As used herein, the terms "target nucleic acid," "target oligonucleotide," and "target polynucleotide," refer to a nucleic acid of interest, e.g., a nucleic acid of a particular nucleotide sequence one wishes to detect and/or quantitate in a sample. The term can refer to a single-stranded or double-stranded polynucleotide molecule (e.g., DNA, RNA, or a combination thereof), or a specific strand thereof, to which a specific oligonucleotide primer, oligonucleotide probe, or combination thereof, anneals or hybridizes. In some embodiments of the aspects described herein, annealing of an oligonucleotide primer to a target nucleic acid under specific conditions permits a polymerase to extend the oligonucleotide primer to form an extension product complementary to the target nucleic acid. A target nucleic acid as used herein has at least a portion of sequence that is complementary to a specific oligonucleotide primer, a specific oligonucleotide probe, or a combination thereof.

As used herein, an "oligonucleotide primer" or "primer" refers to a polynucleotide molecule (i.e., DNA, RNA, or a combination thereof) capable of annealing to a target nucleic acid and providing a 3' end substrate for a polymerase enzyme to produce an enzymatic extension product that is complementary to the target nucleic acid. An oligonucleotide primer can refer to more than one primer and can be naturally occurring, as in, for example, a purified restriction digest, or can refer to a molecule produced synthetically, and can act as a point of initiation for the synthesis of a strand complementary to a target nucleic acid when placed under conditions in which primer extension can be catalyzed. A primer as described herein can be single- or double-stranded. That is, in one embodiment, a primer is not double-stranded. The primer is preferably single-stranded for maximum efficiency in amplification. The conditions for initiation and extension usually include the presence of four different deoxyribonucleoside triphosphates (dNTPs) and a polymerization-inducing agent, such as a DNA polymerase or a reverse transcriptase activity, in a suitable buffer ("buffer" includes substituents which are cofactors, or which affect pH, ionic strength, etc.) and at a suitable temperature. "Primers" useful in the methods described herein are generally less than or equal to 100 nucleotides in length, e.g., less than or equal to 90 nucleotides in length, less than or equal to 80 nucleotides in length, less than or equal to 70 nucleotides in length, less than or equal to 60 nucleotides in length, less than or equal to 50 nucleotides in length, less than or equal to 40 nucleotides in length, less than or equal to 30 nucleotides in length, less than or equal to 20 nucleotides in length, or less than or equal to 15 nucleotides in length, but preferably at least 10 nucleotides in length. The term "primer site" or "primer binding site" refers to the segment of a target nucleic acid to which a primer hybridizes. It is preferred that a primer oligonucleotide anneals or hybridizes to a target nucleic acid under stringent conditions. That is, in some embodiments, a primer oligonucleotide hybridizes to a target nucleic acid under stringent conditions.

As used herein, an "oligonucleotide probe member," "probe member," "probe," or "oligonucleotide probe" refer to an oligonucleotide which anneals to or forms a duplex structure with a sequence in a target nucleic acid, due to complementarity of a sequence in the probe with a sequence in a target region of a target nucleic acid. The sequence that the probe binds or hybridizes to in the target nucleic acid is a "probe binding site." In addition to the nucleic acid sequence complementary to the target nucleic acid, a probe can have at one end an "overhang sequence" that does not hybridize or anneal, i.e., is not complementary, to the target nucleic acid. Such a non-hybridizing overhang sequence has a length of 1 nucleotide or less, 2 nucleotides or less, 3 nucleotides or less, 4 nucleotides or less, 5 nucleotides or less, 6 nucleotides or less, 7 nucleotides or less, 8 nucleotides or less, 9 nucleotides or less, or 10 nucleotides or less. The probe is preferably detectably labeled, as described herein, at the 5' terminal nucleotide when no overhang is present, or to any one of the non-hybridizing overhang nucleotides at the 5' end of a probe when an overhang is present. The probe, preferably, does not contain a sequence complementary to the region of a target nucleic acid sequence(s) to which an oligonucleotide primer binds to in the same reaction. Generally, the 3' terminus of an oligonucleotide probe will be "blocked" to prohibit incorporation of the probe into a primer extension product. "Blocking" can be achieved by using non-complementary bases, as described herein, or by adding a chemical moiety, such as biotin or a phosphate group, to the 3' hydroxyl of the last nucleotide of the oligonucleotide probe, which can, depending upon the selected moiety, serve a dual purpose by also acting as a label for subsequent detection or capture of the nucleic acid attached to the label. Blocking can also be achieved by removing the 3'-OH or by using a nucleotide that lacks a 3'-OH such as a dideoxynucleotide. Oligonucleotide probes useful in the methods described herein are generally less than or equal to 100 nucleotides in length, e.g., less than or equal to 90, less than or equal to 80, less than or equal to 70, less than or equal to 60, less than or equal to 50, less than or equal to 40, less than or equal to 30, less than or equal to 20, or less than or equal to 15 nucleotides in length. Within these general considerations, length of a probe will depend upon nucleotide composition and the conditions under which the probes will be used in a given assay. Specific considerations for probe design and use are described elsewhere herein. It is preferred that a probe oligonucleotide anneals or hybridizes to a probe binding site on a target nucleic acid under stringent conditions.

The term "label" as used herein refers to any atom or molecule that can be used to provide a detectable (preferably quantifiable) signal, and which can be attached to a nucleic acid or protein. Labels can provide signals detectable by fluorescence, radioactivity, colorimetry, gravimetry, X-ray diffraction or absorption, magnetism, enzymatic activity, mass spectrometry, binding affinity, hybridization radiofrequency, nanocrystals and the like. Accordingly, a "detectably labeled nucleotide" (e.g., a NTP or dNTP), or "detectably labeled oligonucleotide," such as an oligonucleotide probe, is one linked to a detectable label. Fluorescent labels are preferred in the methods described herein. The term "linked" encompasses covalent and non-covalent bonding, e.g., by hydrogen, ionic, or Van der Waals bonds. The terms "detectable label" or "label" can also include a molecule or moiety capable of generating a detectable signal through the interaction with another label. Such a label can be a member of a signal generating system, and thus can generate a detectable signal in context with other members of the signal generating system, e.g., a biotin-avidin signal generation system, or a donor-acceptor pair for fluorescent resonance energy transfer (FRET) (Stryer et al., 1978, Ann. Rev. Biochem., 47:819; Selvin, 1995, Methods Enzymol., 246:300). In preferred embodiments, the label does not comprise a donor/acceptor pair for FRET. A "label," as that term is used herein, causes anomalous migration (as that term is defined herein) of a nucleic acid or nucleotide to which it is linked, especially with regard to short nucleic acid sequences, e.g., 0-10 nucleotides, bearing the label.

As noted above, a fluorescent dye is a preferred label according to the methods described herein. Examples of fluorescent dyes include, but are not limited to, fluorochromes such as cyanines (e.g., CY3, CY3.5, CY5, CY5.5, CY7, etc., see Published International Application No. WO 97/45539 by Kubista), rhodamine and derivatives (such as Texas Red, R6G, R110, TAMRA, ROX, etc., see U.S. Pat. Nos. 5,366,860; 5,847,162; 5,936,087; 6,051,719; 6,191,278,), fluorescein and derivatives (such as 5-bromomethyl fluorescein, 2',7'-dimethoxy-4',5'-dichloro-6-carboxyrhodamine (JOE), 6-carboxylfluorescein (6-FAM), 1,2',4',1,4,-tetra chlorofluorescein (TET), 2',4',5',7',1,4-hexa chlorofluorescein (HEX), see U.S. Pat. Nos. 5,188,934; 6,008,379; 6,020,481), Lucifer Yellow, IAEDANS, benzophenoxazines (U.S. Pat. No. 6,140,500), 7-$Me_2$N-coumarin-4-acetate, 7-OH-4-$CH_3$-coumarin-3-acetate, 7-$NH_2$-4-$CH_3$-coumarin-3-acetate (AMCA), monobromobimane, pyrene trisulfonates, such as Cascade Blue, Oregon Green, and monobromorimethyl-ammoniobimane (see for example, DeLuca, Immunofluorescence Analysis, in Antibody As a Tool, Marchalonis et al., eds., John Wiley & Sons, Ltd., (1982), which is incorporated herein by reference). Additional examples of fluorescent dyes are provided in, e.g., Haugland, Molecular Probes Handbook of Fluorescent Probes and Research Products, Ninth Ed. (2003) and the updates thereto, which are each incorporated by reference. Fluorescent dyes are generally readily available from various commercial suppliers including, e.g., Molecular Probes, Inc. (Eugene, Oreg.), Amersham Biosciences Corp. (Piscataway, N.J.), Applied Biosystems (Foster City, Calif.), etc. Fluorescein dyes and derivatives thereof are particularly preferred in the methods described herein.

A "polymerase" refers to an enzyme that catalyzes polynucleotide synthesis by addition of nucleotide units to a nucleotide chain using DNA or RNA as a template. The term refers to either a complete enzyme as it occurs in nature or an isolated catalytic domain, or fragment thereof having polymerase activity. Generally, the polymerase enzyme will initiate synthesis at the 3'-end of a primer annealed to a template target sequence, and will proceed in the 5'-direction along the target nucleic acid to synthesize a strand complementary to the target nucleic acid until synthesis terminates. In aspects described herein, it is desirable that the polymerase further possesses 5' to 3' exonuclease activity, whereby a polynucleotide (e.g., a oligonucleotide probe), annealed downstream of and on the same strand as an extending oligonucleotide primer, is hydrolyzed or cleaved by the polymerase's 5' to 3' activity, releasing probe fragments, including labeled fragments or nucleotides, as hydrolysis continues.

As used herein, the term "thermostable nucleic acid polymerase" refers to an enzyme that is relatively stable to heat when compared, for example, to nucleotide polymerases from *E. coli*, and which catalyzes the template-dependent polymerization of nucleoside triphosphates. A "thermostable nucleic acid polymerase," as the term is used herein, will retain enzymatic activity for polymerization and exonuclease activities when subjected to the repeated heating and cooling cycles used in PCR. Preferably, a "thermostable nucleic acid polymerase" has optimal activity at a temperature above 45° C. A representative thermostable polymerase enzyme isolated from *Thermus aquaticus* (Taq) is described in U.S. Pat. No. 4,889,818 and a method for using it in conventional PCR is described in Saiki et al., 1988, Science 239:487. Taq DNA polymerase has a DNA synthesis-dependent, strand displacement 5'-3' exonuclease activity (see Gelfand, "Tag DNA Polymerase" in PCR Technology; Principles and Applications for DNA Amplification, Erlich, Ed., Stockton Press, N.Y. (1989), Chapter 2). In solution, there is little, if any, degradation of labeled oligonucleotides by a thermostable nucleic acid polymerase useful in the methods and compositions described herein.

The terms "5' to 3' exonuclease," "5' to 3' exonuclease activity," or "5' to 3' nuclease activity" refers to a protein or domain of, or a protein activity of, a protein that catalyzes the stepwise removal of mononucleotides or short oligonucleotides, e.g., 2 nucleotides to 3 nucleotides long, from 5'-termini of DNA molecules. "5' to 3' exonuclease activity" includes a 5' to 3' exonuclease activity traditionally associated with some DNA polymerases, whereby nucleotides are removed from the 5' end of an oligonucleotide annealed to a template or target nucleic acid in a sequential manner. A 5' to 3' exonuclease activity useful in the methods described herein does not catalyze the hydrolysis of oligonucleotide probe molecules that are not annealed to a target nucleic acid.

As used herein, any fragment of an annealed or target-bound oligonucleotide probe, released by the 5' to 3' exonuclease activity of a polymerase, which comprises both the label and at least one nucleotide of the oligonucleotide probe, is termed a "labeled detection molecule." In some embodiments of the aspects described herein, such a "labeled detection molecule" further comprises one or more nucleotides comprised by a 5' overhang of the oligonucleotide probe. In preferred embodiments of the aspects described herein, such labeled detection molecules exhibit or are characterized by an anomalous migration pattern upon separation, as defined herein.

As used herein, "hybridizing" or "annealing" refer to the hydrogen-bonded base-pairing interaction of one oligonucleotide with another oligonucleotide (typically an antiparallel polynucleotide) that results in formation of a duplex, typically termed a "hybridization complex" or a "hybridized duplex." The ability of two oligonucleotide sequences to hybridize is a function of not only the complementarity of the two sequences, but also includes such factors as the temperature under which the two sequences are contacted (higher temperatures inhibit annealing of oligonucleotides), the pH and concentrations and identities of the salt(s) in the reaction mixture, and the concentrations of the respective oligonucleotides. It is not a requirement that two oligonucleotides have 100% complementarity over their full length to achieve hybridization. However, the greater the degree of complementarity, the greater the ability of two sequences to hybridize under what are termed "stringent hybridization conditions."

When two different, non-overlapping oligonucleotides, such as a primer and a probe as described herein, anneal or hybridize to different regions of the same linear complementary target nucleic acid sequence, and the 3' end of the first oligonucleotide points toward the 5' end of the other, second oligonucleotide, the former can be called the "upstream" oligonucleotide and is considered "5'" of the second oligonucleotide, and the latter the "downstream" oligonucleotide and is "3'" of the first oligonucleotide.

The term "adjacent" as used herein refers to the position of the 5' end of an annealed probe relative to the 3' end of an annealed primer or its extension product. The 3' end of a primer or its extension product is said to be "adjacent" to the 5' end of an annealed probed when the 5' to 3' exonuclease activity of the polymerase used in a given assay can cleave one or more nucleotides from the 5' end of the annealed probe. Where cleavage is polymerization independent, this will generally be 0 (immediately adjacent) to 10 or 20 nucleotides upstream of the annealed probe, depending upon the 5' to 3' exonuclease activity of the polymerase chosen. Where cleavage is polymerization dependent, the primer can anneal upstream of the probe, and the primer's extended 3' end will be adjacent to the 5' end of the probe when the 5' to 3' exonuclease activity of the polymerase is close enough to cleave the 5' end of the probe.

As used herein, "isolated" or "purified" when used in reference to a polynucleotide means that a naturally occurring sequence has been removed from its normal cellular environment or is in a non-natural environment. Thus, an "isolated" or "purified" sequence can be in a cell-free solution or placed in a different cellular environment. The term "purified" does not imply that the sequence is the only polynucleotide present, but that it is essentially free (about 90-95%, up to 99-100% pure) of non-nucleotide or polynucleotide material naturally associated with it.

As used herein, "extending" refers to any template-dependent, enzymatic, in vitro method for making a new strand of polynucleotide or elongating an existing polynucleotide (i.e., DNA or short RNA). The act of extending according to the methods described herein, can include amplification, which increases the number of copies of a polynucleotide template sequence with the use of a polymerase. Extending a polynucleotide results in the incorporation of nucleotides into a polynucleotide sequence, thereby forming an extended polynucleotide molecule complementary to the polynucleotide template.

The term "replication reaction" refers to an in vitro means for making a single copy of a target sequence of nucleic acid, i.e., where amplification of a target nucleic acid sequence does not occur. "Replicating" refers to a step of submitting a solution to conditions sufficient to allow for replication of a polynucleotide, if all of the components of the reaction are intact. Components of a replication reaction include, e.g., a primer, a polynucleotide template, polymerase, nucleotides, and the like. Accordingly, the term "replication reaction mixture" refers to an aqueous solution comprising the various reagents used to copy a target nucleic acid. These include components such as enzymes, aqueous buffers, salts, amplification primers, target nucleic acid, and nucleoside triphosphates.

The term "amplification reaction" refers to an in vitro process for providing multiple copies of a target sequence of nucleic acid, i.e., where more than one copy of a target nucleic acid sequence is made. "Amplifying" refers to a step of subjecting nucleic acids in a solution to conditions sufficient to allow for amplification of a target nucleic acid polynucleotide, if all of the components of the reaction are intact. Components of an amplification reaction include, e.g., primers, a polynucleotide template, polymerase, nucleotides, and the like. The term "amplifying" typically refers to an "exponential" increase the number of copies of a target nucleic acid. However, "amplifying" as used herein can also refer to linear increases in the number of copies of a select target sequence of nucleic acid. Accordingly, the term "amplification reaction mixture" refers to an aqueous solution comprising the various reagents used to amplify a target nucleic acid. These include components such as enzymes, aqueous buffers, salts, amplification primers, target nucleic acid, and nucleoside triphosphates. Depending upon the context, the mixture can be either a complete or incomplete amplification reaction mixture "Polymerase chain reaction" or "PCR" refers to a method whereby a specific segment or subsequence of a target nucleic acid, is amplified in a geometric progression, using repeated cycles of primer annealing, primer extension, and thermal strand separation. PCR is well known to those of skill in the art; see, e.g., U.S. Pat. Nos. 4,683,195 and 4,683,202; and PCR Protocols: A Guide to Methods and Applications, Innis et al., eds, 1990; Sambrook and Russell, MOLECULAR CLONING, A LABORATORY MANUAL (3rd ed. 2001); and CURRENT PROTOCOLS IN MOLECULAR BIOLOGY (Ausubel et al., eds., John Wiley & Sons, Inc. 1994-1997, 2001 version).

"Multiplex amplification" refers to amplification of multiple different target nucleic acid sequences in the same reaction (see, e.g., PCR PRIMER, A LABORATORY MANUAL (Dieffenbach, ed. 1995) Cold Spring Harbor Press, pages 157-171). "Multiplex amplification," as used herein, refers to amplification of at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 30 or more targets, e.g., at least 50, at least 100, at least 250 or more targets.

As used herein, "electrophoresis" refers to analytical techniques for separating nucleic acids, or molecules comprising nucleic acids, such as the labeled detection molecules described herein, using an electric field to cause migration of negatively charged nucleic acids (due to the net negative charge of the phosphate backbone of the nucleic acid chain) towards a positive potential or anode. Separation of these nucleic acids and their fragments is accomplished by exploiting the differential mobilities or migrations of different sized nucleic acid molecules within a substrate, such as a gel or capillary system. In general, longer nucleic acid molecules migrate more slowly because they experience more resistance or friction. Because the size of a nucleic acid molecule affects its mobility, smaller nucleic acid fragments end up nearer to the anode than longer ones in a given period of a time. Molecules that exhibit anomalous migration as described herein do not strictly follow this rule. Electrophoresis can be performed using a variety of methods known to one of skill in the art, including, but not limited to slab gel electrophoresis, capillary electrophoresis (CE), and matrix-embedded microfluidic channels. To the extent that anomalous migration occurs using other separation methods, such separation methods are also contemplated for use with the methods described herein.

As used herein, "anomalous migration" refers to a migration pattern of a nucleic acid or a molecule comprising a nucleic acid, such as the labeled detection molecules described herein, wherein a larger nucleic acid, or a molecule comprising such a nucleic acid, migrates faster during electrophoresis than a corresponding smaller nucleic acid, under the same separation conditions. For example, the labeled detection molecules described herein, which comprise a label and at least one nucleotide of an oligonucleotide probe, have anomalous migration patterns, such that a labeled detection molecule comprising a label and 6 nucleotides migrates faster than a labeled detection molecule comprising the same label and 3 nucleotides, under the same conditions of separation.

The practice of the present invention will employ, unless otherwise indicated, conventional techniques of molecular biology, microbiology and recombinant DNA techniques, which are within the skill of the art. Such techniques are explained fully in the literature. See, e.g., Sambrook, Fritsch & Maniatis, Molecular Cloning; A Laboratory Manual, Second Edition (1989); Oligonucleotide Synthesis (M. J. Gait, ed., 1984); Nucleic Acid Hybridization (B. D. Hames & S. J. Higgins, eds., 1984); A Practical Guide to Molecular Cloning (B. Perbal, 1984); and a series, Methods in Enzymology (Academic Press, Inc.). All patents, patent applications, and publications mentioned herein, both supra and infra, are hereby incorporated by reference.

BRIEF DESCRIPTION OF THE DRAWINGS

In the experiments described in FIGS. 1A-1F, which demonstrate detection of fluorophore labeled non-target sequence products, the TaqMan™-style assays comprised: primers specific for amplification of a desired target nucleic acid sequence; an oligonucleotide probe that annealed to its probe binding site within the target sequence amplified by the primers, where the oligonucleotide probe comprised a fluorophore covalently attached to its 5'-end, such as 6-carboxyfluorescein (FAM); a polymerase having 5' to 3' exonuclease activity, such as HotStar Taq polymerase or AmpliTaq Gold® DNA polymerase; and appropriate reagents for the amplification reaction, including nucleotides and buffers. Further, the oligonucleotide probes used had complete complementarity to their probe binding sites. In some experiments, the forward primer was labeled with a TYE label, as illustrated in FIG. 1A. In these experiments, it was surprisingly found that all the tested TaqMan assays generated FAM-labeled products with approximate apparent sizes of 50 and 95 bp, regardless of the target nucleic acid sequence being amplified, in addition to the TYE-labeled amplified target sequence.

(FIGS. 2A-2B) and HHV6 (FIGS. 2C-2D), FAM-labeled PCR products were not observed.

As shown in FIGS. 4A-4B, when HotStar Taq or AptaTaq were used as the polymerases in the amplification reactions, both of which possess 5' to 3' exonuclease activity, an additional FAM-labeled product was detected, in addition to the TYE-labeled amplified target sequence. However, when polymerases lacking 5' to 3' exonuclease activity were utilized, such as Pfu and PyroPage exo-, no additional FAM-labeled product was detected, as shown in FIGS. 4C-4D.

As shown in FIG. 5, in contrast to larger nucleotides, the FAM-labeled synthetic nucleotides demonstrated anomalous migration, such that largest labeled synthetic oligonucleotide migrated the fastest, and the smallest labeled synthetic oligonucleotide migrated the slowest.

FIG. 6C demonstrates that, with increasing lengths of the overhang sequence or mismatch at the 5' end, the faster the labeled detection molecules generated migrated, i.e., anomalous migration.

DETAILED DESCRIPTION

Figures 1A, 1B:
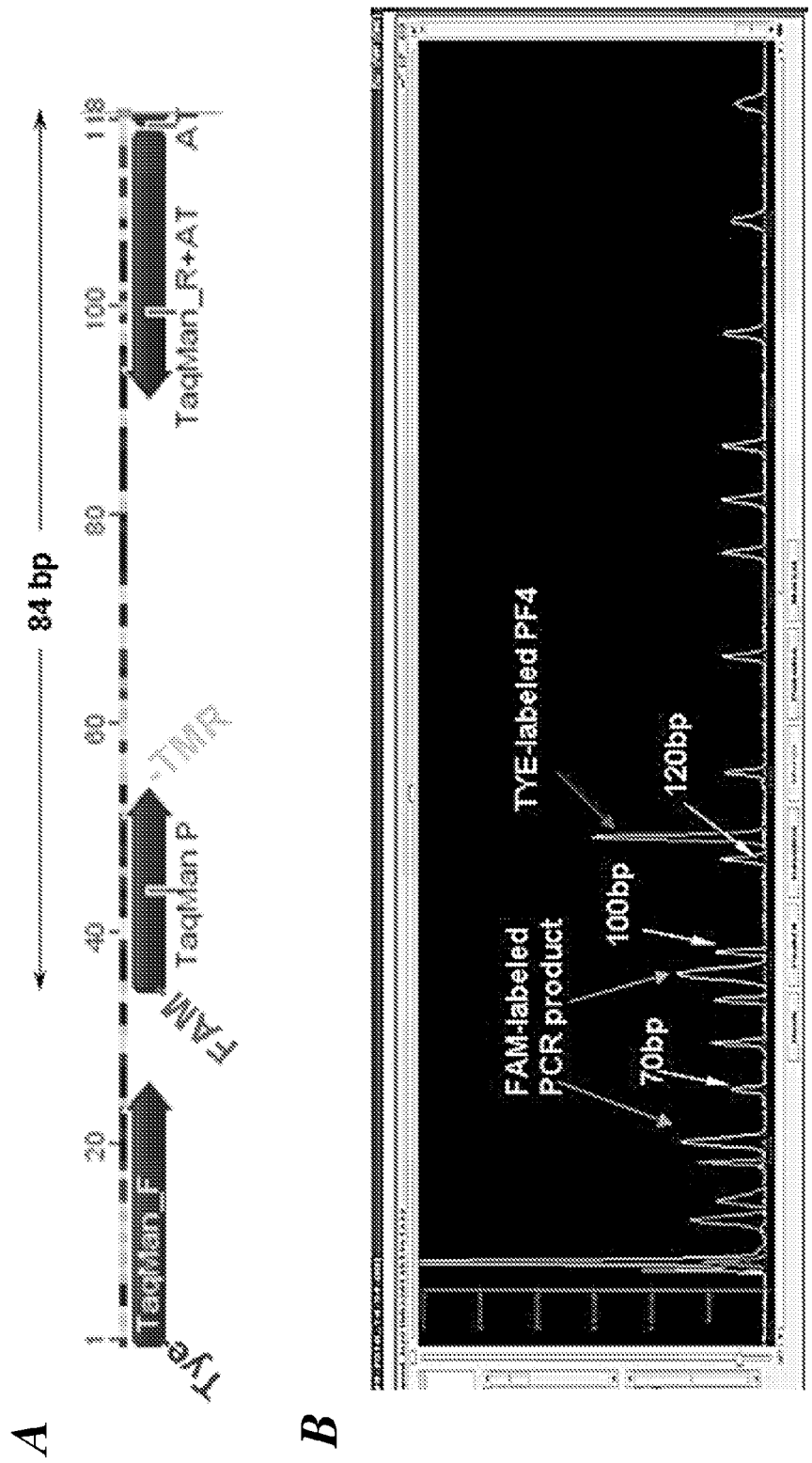
FIGS. 1A-1B demonstrates the generation of fluorophore-labeled products when the target sequence was PF4.
Figure 1C:
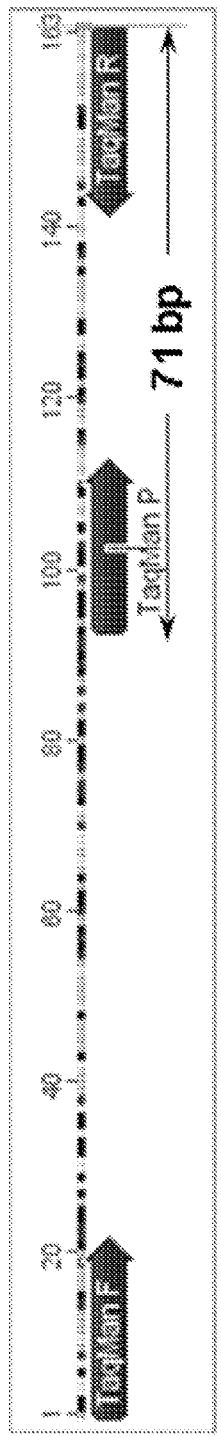
FIGS. 1C-1D demonstrate the generation of fluorophore-labeled products when the target sequence was CMV, and FIGS. 1E-1F demonstrate the generation of fluorophore-labeled products when the target sequence was EBV. These products and their corresponding peaks were found to be reproducible and specific, demonstrated dose response to target concentrations, and demonstrated low copy number assay sensitivity. In the FIGS. 1B, 1D and 1F, PCR product was spiked with FAM-labeled DNA ladder prior to subjecting to CE separation.

Provided herein are approaches for the detection and quantification of nucleic acids in a sample. The methods permit the detection of individual species of target nucleic acids in a sample, both singly and by using multiplex formats that detect and quantify two or more species of target nucleic acids in a single reaction. These approaches are based, in part, on the elucidation of anomalous migration properties of nucleic acid molecules, and particularly short nucleic acid molecules, conjugated to a fluorescent label, such as FAM (fluorescein amidite) and derivatives thereof. The approaches described herein permit the identification and quantification of target nucleic acids in a sample by detecting and quantifying a labeled product generated by the 5' to 3' nuclease activity of a nucleic acid polymerase on a detectably labeled oligonucleotide probe hybridized to a target nucleic acid. These methods can be used on unamplified or amplified target nucleic acid species, and in singleplex or multiplex formats, using size separation based methods, such as capillary electrophoresis, coupled with detection by, for example, fluorescence detection.

Target Nucleic Acid Detection

There are essentially two different types of detection strategies applied to nucleic acid molecule in vitro assays. In the first, generally referred to as "homogenous" assays, there is no separation of the nucleic acid species necessary for detecting and or quantifying the target nucleic acid. In the second, commonly referred to as "non-homogenous" approaches, a separation step is employed. The separation can be, for example, by size or charge, as for electrophoretic separation, or can exploit other physical differences between the target species. Hybridization to an immobilized probe, e.g., on a microarray, also constitutes a type of separation that can be used in a non-homogenous assay.

A variety of techniques for semi-quantitative and quantitative detection of amplified nucleic acids have been described. These techniques include 5' to 3' exonuclease assays, e.g., the so-called Taqman™ assay (see, e.g., U.S. Pat. Nos. 5,210,015 and 5,487,972, Heid et al., Genome Res. 6:986-994, 1996; Holland et al., Proc. Nat'l Acad. Sci. USA 88:7276-7280, 1991; and Lee et al., Nuc. Acids Res. 21:3761-3766, 1993), and assays that depend upon interactions or changes in interactions between a pair of fluorophores or a fluorophore and a quencher on one or more oligonucleotide probes. See, e.g., U.S. Pat. No. 6,174,670, U.S. Pat. No. 5,989,823, and U.S. Pat. No. 6,326,145, each of which is herein incorporated in their entireties by reference.

The methods described herein provide novel ways of quantifying and detecting nucleic acids, and are particularly well-suited for the specific detection of amplified nucleic acid products. The various aspects described herein are based, in part, on recognition and elucidation of reliable yet, anomalous migration properties of labeled detection molecules as described herein. These methods employ a labeled oligonucleotide probe, which can be used in a replication and/or amplification reaction for a target nucleic acid species with a polymerase and an enzyme that has 5' to 3' exonuclease activity. In the methods described herein, the 5' to 3' exonuclease activity of a polymerase is used to generate labeled detection molecules which have anomalous migration properties. The 5' to 3' nuclease activity of the polymerase can cleave mononucleotides or small oligonucleotides from an oligonucleotide, such as a labeled oligonucleotide probe, annealed to its larger, complementary polynucleotide. In some embodiments of the aspects described herein, the labeled oligonucleotide comprises a 5' non-complementary overhang sequence. In order for cleavage to occur efficiently, an upstream oligonucleotide, such as an oligonucleotide primer, must also be annealed to the same larger polynucleotide. The 3' end of this upstream oligonucleotide provides the initial binding extension site for the nucleic acid polymerase. When the bound polymerase encounters the 5' end of the downstream oligonucleotide, the polymerase can cleave mononucleotides or small oligonucleotides from it.

In some aspects of the methods described herein, the two oligonucleotides, i.e., the primer and the labeled probe, can be designed such that they anneal in close proximity on a complementary target nucleic acid, such that binding of a nucleic acid polymerase to the 3' end of the upstream oligonucleotide automatically puts it close enough to contact the 5' end of the downstream labeled oligonucleotide probe to cleave the probe without polymerization. This process, because polymerization is not required to bring the nucleic acid polymerase into position to accomplish the cleavage, is termed herein "polymerization-independent cleavage."

Alternatively, in other aspects of the methods described herein, if the two oligonucleotides anneal to more distantly spaced regions of the template nucleic acid target, polymerization must occur before the nucleic acid polymerase encounters the 5' end of the downstream labeled oligonucleotide probe. In such aspects, the nucleic acid polymerase binds to the 3' end of the upstream oligonucleotide primer and extends the primer sequence by generating a polynucleotide sequence complementary to the target nucleic acid to which the upstream primer is bound. As the polymerization or extension continues, the polymerase encounters the downstream labeled oligonucleotide probe and progressively cleaves mononucleotides or small oligonucleotides from its 5' end, thus producing labeled detection molecules of a specific size. This cleaving continues until the remainder of the downstream oligonucleotide has been destabilized to the extent that it dissociates from the template molecule. This process is termed herein as "polymerization-dependent cleavage."

Subsequently, electrophoretic methods, such as capillary gel electrophoresis, can be employed, to distinguish uncleaved labeled oligonucleotide probes from the labeled detection molecules thereof. In this manner, the methods described herein permit identification, detection, and quantitation of those nucleic acid samples which contain sequences complementary to the upstream and downstream oligonucleotides.

Elucidated Rule or Key for Probe Read-Out:

The methods described herein benefit from the application of a "rule" or "key" that permits the assignment of anomalous migrating labeled fragments to their respective signal peaks. It is recognized herein that signal peaks previously thought to be artifacts (see, e.g., Asuragen Inc.'s BCR/ABL1 Quant Kit white paper on the world wide wibe at asuragen.com/pdfs/Dx/2500-0166_BCR_ABL_whitepaper.pdf, which is herein incorporated by reference in its entirety) in fact correspond to specific species of nucleic acids generated in "TaqMan style" assays, and that the anomalous migration can be harnessed to provide sensitive quantitation of target nucleic acids, and manipulated to provide increased multiplex detection opportunities.

In order to assign a fluorescent signal from a labeled detection molecule separated by electrophoresis to a specific target, the following described rule is applied. A dye or label, e.g., FAM, plus six nucleotides migrates faster than or with increased mobility relative to the dye plus five nucleotides, which migrates faster than or with increased mobility relative to the dye plus four nucleotides, which migrates faster than or with increased mobility relative to the dye plus three nucleotides, which migrates faster than or with increased mobility relative to the dye plus two nucleotides, which migrates faster than or with increased mobility relative to the dye plus one nucleotide, which migrates faster than or with increased mobility relative to the free dye or label. For oligonucleotides larger that six nucleotides, the migration pattern becomes a substantially linear relationship, with, for example, dye-labeled 8-mer oligonucleotide migrating faster than a dye-labeled 10-mer oligonucleotide, and a dye-labeled 10-mer oligonucleotide migrating faster than a dye-labeled 20-mer oligonucleotide. For example, FAM label plus 1 nucleotide routinely runs at approximately the position of a FAM-labeled 95-base polynucleotide.

To the extent that different dyes cause anomalous migration of small cleavage products to different extents, the ordinarily skilled artisan can develop a key for each dye label of interest by capillary electrophoretic separation of fragments of known sizes labeled with the dye of choice. For example, dye-labeled 1-mer, 2-mer, 3-mer, 4-mer, 5-mer, 6-mer, or more, can be individually separated by capillary electrophoresis, and migration time past a detector noted. The relative migration and inflection point at which increasing size begins to correlate with decreased mobility for a single dye provide the keys to peak alignments for fragments smaller than the size at the inflection point. By manipulation of the 5' overhang on a labeled probe, one can manipulate that length of fragments generated by the 5' to 3' exonuclease activity of a polymerase. The use of labeled probes of varying overhang lengths combined with the rules described herein for the anomalous migration and peak assignment permit a higher degree of multiplex for assays that depend upon the 5' to 3' exonuclease activity, e.g., TaqMan-style assays, and assays as described herein.

The methods described herein can also be used to exploit the anomalous migration properties of labeled detection molecules when used in conjunction with PCR. These methods differ from previously described quantitative PCR amplification methods, where the detection of the target nucleic acid sequences occurs during amplification of the target nucleic acids. In the methods described herein, labeled oligonucleotide probes having 5', non-hybridizing overhang sequences, are added concomitantly with the primer at the start of the amplification, and both the signal generated from hydrolysis of the labeled oligonucleotide probe and anomalous migration of the labeled detection molecule, which is dependent on the size of the 5' overhang sequence, provide a means for detection and quantitation of the target nucleic acid sequence. Thus, in such aspects, PCR amplification can be conducted using different PCR primer pairs and labeled oligonucleotide probes, producing PCR products of different sizes, which are specific for or correlate with specific target nucleic acids being amplified, as well as different sized labeled detection molecules having anomalous migration properties. The amplified PCR products and labeled detection molecules can be separated by methods providing size discrimination, such as electrophoresis. The labeled detection molecules can be detected by, for example, fluorescence detection.

The methods described herein are also compatible with other amplification systems, such as the transcription amplification system, in which two different enzymes are used to drive amplification. The first enzyme is a reverse transcriptase that creates a double-stranded DNA copy from an RNA or DNA template. The second enzyme, an RNA polymerase, makes thousands of copies of the complementary RNA sequence known as the 'RNA amplicon', from the double-stranded DNA template. Each RNA amplicon serves as a new target for the reverse transcriptase and the process repeats automatically, resulting in an exponential amplification of the original target that can produce over a billion copies of amplicon in less than 30 minutes. By incorporating a polymerase with 5' to 3' exonuclease activity into a ligase chain reaction (LCR) system, together with appropriate oligonucleotides, one can also employ the methods described herein to detect LCR products.

In some aspects, the methods described herein can be applied to systems that do not involve amplification. In fact, as noted above, in some embodiments the methods do not require that polymerization occur. One advantage of polymerization-independent processes lies in the elimination of the need for amplification of the target nucleic acid sequence. In the absence of primer extension, the target nucleic acid is substantially single-stranded. Provided the primer and labeled oligonucleotide are adjacently bound, as the term is defined herein, to the target nucleic acid, sequential rounds of oligonucleotide annealing and cleavage of labeled detection molecules can occur. Thus, a sufficient amount of labeled detection molecules can be generated, making detection possible in the absence of polymerization. As would be appreciated by those skilled in the art, the signal generated during PCR amplification could be augmented by this polymerization-independent activity.

The components and steps of the methods described herein are provided in more detail below.

Samples

For the methods described herein, a sample is provided that is suspected to or presumed to contain or comprise the particular target nucleic acid sequence of interest. Such a sample includes, for example, a cellular extract, or a tissue extract or fluid extract isolated from an individual(s) or organism, or any polynucleotide(s) purified or isolated from such cellular, tissue, or fluid extracts, including, but not limited to, skin, plasma, serum, spinal fluid, lymph fluid, synovial fluid, urine, tears, blood cells, organs, tumors. Nucleic acid samples can also be extracted or isolated from in vitro cell culture constituents, such as conditioned medium resulting from the growth of cells (including prokaryotic and eukaroyotic cells) in cell culture medium, recombinant cells, and cell components. In some embodiments, a sample can be obtained from an environmental source.

A sample comprising a target nucleic acid can, in some embodiments, be first reverse transcribed into cDNA, if necessary, and then denatured, using any suitable denaturing method, including physical, chemical, or enzymatic means, which are known to those of skill in the art. A preferred physical means for strand separation involves heating the nucleic acid until it is completely (>99%) denatured. Typical heat denaturation involves temperatures ranging from about 80° C. to about 105° C., for times ranging from a few seconds to minutes. As an alternative to denaturation, the target nucleic acid can exist in a single-stranded form in the sample, such as, for example, nucleic acid samples obtained from single-stranded RNA or DNA viruses.

In most instances, there will need to be a step of isolating nucleic acid from a given sample source, to provide nucleic acids comprising target nucleic acids of interest, in a form accessible to methods described herein. Typically, these methods of isolation comprise cell lysis, followed by purification of polynucleotides by methods such as phenol/chloroform extraction, electrophoresis, and/or chromatography. Often, such methods include a step where the polynucleotides are precipitated, e.g. with ethanol, and resuspended in an appropriate buffer for primer extension, or similar reaction.

In certain embodiments of the aspects described herein, two or more target nucleic acid sequences from one or more sample sources are analyzed in a single reaction. In some applications, a single polynucleotide from a multitude of sources can be synthesized to screen for the presence or absence of a particular sequence. In other applications, a plurality of polynucleotides can be generated from a single sample or individual, thereby allowing the assessment of a variety of polynucleotides in a single sample, e.g., to simultaneously screen for a multitude of disease markers in an individual. Any of the above applications can be easily accomplished using the methods described herein. Thus, a reaction mixture can comprise one target polynucleotide, or it can comprise two or more different target polynucleotides.

Primers

Following the denaturation steps, denatured nucleic acid strands are incubated with preselected oligonucleotide primers under hybridization conditions that permit the binding of the primers to the single nucleic acid strands. As known in the art, where target amplification is desired, the primers are selected so that their relative positions along a duplex sequence are such that an extension product synthesized from one primer, when the extension product is separated from its template or complement, serves as a template for the extension of the other primer to yield a replicate chain of defined length. An optimal oligonucleotide primer set for use with the methods described herein should hybridize efficiently to the target nucleic acid sequence of interest with negligible hybridization to other sequences present in a sample.

As used herein, a "primer" refers to a polynucleotide sequence that hybridizes to a sequence on a target nucleic acid template and serves as a point of initiation of nucleic acid synthesis. In the methods described herein, a primer is a component in a replication or amplification reaction that participates in the replication or amplification of the target nucleic acid. The primer must be sufficiently long to prime the synthesis of extension products in the presence of the agent for polymerization, i.e., the polymerase. The exact length and composition of the primer can depend on many factors, including temperature of the annealing reaction, source and composition of the primer, proximity of a desired labeled oligonucleotide probe annealing site to the primer annealing site, and ratio of primer:probe concentration. The length and sequences of primers for use in PCR can be designed based on principles known to those of skill in the art, see, e.g., Innis M A and Gelfand D H (1990; "Optimization of PCRs." In: PCR protocols. A guide to methods an applications. Academic Press, Inc, Chapter 1:3-12.). If there are reasonable amounts of template available, hybridization specificity can be tested by performing the oligonucleotide hybridization. The distance between the oligonucleotide primers can be flexible, and can range up to 10 kb. There can be a drop-off in synthesis efficiency with distances >3 kb (Jeffreys A J et al., 1988; Nucleic Acids Res. 1988 Dec. 9; 16(23):10953-71).

Oligonucleotide primers for use in the methods described herein can be prepared using any suitable method known to those skilled in the art, such as, for example, methods using phosphotriesters and phosphodiesters. In some embodiments of the methods, one or more phosphorothioate linkages can be included in the primers. The oligonucleotide primer can also be modified at the base moiety, sugar moiety, or phosphate backbone with minor groove binders, intercalating agents and the like, so long as its ability to specifically bind template and serve as substrate for polymerase extension (for those embodiments requiring extension) are maintained.

The primers for the replication and amplification reactions can be designed according to known algorithms. Where amplification is desired, the primers are designed to hybridize to sequences that flank the target nucleic acid sequence. Typically, commercially available or custom software use algorithms to design primers such that the annealing temperatures of the primers are close to melting temperature. Primers can be of a variety of lengths and are preferably less than 50 nucleotides in length, more preferably 12-30 nucleotides or bases, and most preferably 15-25 nucleotides in length. Oligonucleotide primers are usually at least 12 bases, more often about 15, about 16, about 17, about 18, about 19, about 20, about 21, about 22, about 23, about 24, or about 25 bases in length. Primers are typically designed so that all primers participating in a particular reaction have melting temperatures that are within 10° C., preferably within 5° C., and most preferably within 2° C. of each other. Primers are further designed to avoid priming on themselves or another primer as templates in a reaction, and to avoid intra- and intermolecular complementarity. In some embodiments, the oligonucleotide primers for use in the methods described herein have a GC content similar to that of the template target nucleic acid. It is preferred that oligonucleotide primers do not comprise unusual sequence distributions, such as stretches of polypurines or polypyrimidines, as such stretches can result in secondary structures that inhibit amplification steps, such as PCR. It is also preferred a given set of oligonucleotide primers do not have complementarity to each other in their 3' ends.

The primers must be sufficiently complementary to anneal to their respective target nucleic acid strands selectively and form stable duplexes. In some embodiments, oligonucleotide primers are designed to be exactly complementary to a template or target nucleic acid sequence. In other embodiments, base-pair mismatches or sites of non-complementarity can be included, e.g., to detect gene homologs where sequence information is lacking. In those embodiments where one or more mismatches are to be included in an oligonucleotide primer set, it is preferred that the mismatches or non-complementary sites occur at the 5' end of the primer, as the closer a mismatch is to the 3' end of a primer, the more likely it is to prevent extension of the annealed primer.

In the case of an amplification reaction, primer concentration should be sufficient to bind to the amount of target sequences that are amplified, so as to provide an accurate assessment of the quantity of amplified sequence. Those of skill in the art will recognize that the amount or concentration of primer will vary according to the binding affinity of the primers as well as the quantity of sequence to be bound. Typical primer concentrations range from 0.01 µM to 1.0 µM.

The replication and amplification reactions described herein are performed under conditions in which the primers hybridize to the target sequence template and are extended by a polymerase. As appreciated by those of skill in the art, such reaction conditions can vary, depending on the target nucleic acid of interest and the composition of the primer. Replication and amplification reaction cycle conditions are selected so that the primers hybridize specifically to the target template sequence and are extended. Primers that hybridize specifically to a target template amplify the target sequence preferentially in comparison to other nucleic acids that may be present in the sample that is analyzed.

Specific oligonucleotide pairs for use in amplification from an RNA template are designed and utilized with many of the same considerations discussed herein for enzymatic amplification of DNA. In some embodiments of the aspects described herein, increased specificity can be gained by using an additional primer, internal to that used for cDNA synthesis, for subsequenct PCR amplification. Moreover, in some embodiments, reamplification with nested primers can be used for RNA amplification. In some embodiments, primers for RNA amplification can be designed and chosen such that specific amplification products cannot arise from DNA. For example, primers from different exons will yield products of different sizes depending on whether a cell's DNA or mRNA is used as a template. In other cases, it will not be possible to select such discriminatory primers, and therefore enzymatic treatment of samples with RNase-free DNase, followed by phenol extraction and ethanol precipitation, can be used to ensure amplification products are generated from only RNA target nucleic acid sequences.

Oligonucleotide Probes and Probe Labels

An oligonucleotide probe for use in the methods described herein can be any suitable size determined by one of skill in the art, and are often in the range of from about 6 to about 100 nucleotides or bases, more often from about 6 to about 80 nucleotides, and most frequently from about 10 to about 40 nucleotides. As used herein a "probe" or "oligonucleotide probe" refers to a polynucleotide sequence capable of hybridization to a target polynucleotide sequence of interest, and that allows for the specific detection of a target polynucleotide sequence of choice. The oligonucleotide probe is typically labeled with a detectable moiety. The detectable moiety can be any moiety that directly or indirectly results in a change in signal when it is cleaved, and which has or confers an anomalous migration property, as that term is defined herein.

The precise sequence and length of an oligonucleotide probe depends in part on the nature of the target polynucleotide sequence to which it binds. The binding location and length can be varied to achieve appropriate annealing and melting properties for a particular embodiment. Guidance for making such design choices can be found in many art recognized references. Hybridization of the probe, in conjunction with replication and/or amplification of the target sequence with oligonucleotide primers to replicate or amplify the template nucleic acid sequence, can be used to provide a determination of the presence and/or amount of a target nucleic acid sequence in a sample.

The oligonucleotide probe can be extended during the course of the amplification upon cleavage of the 5' nucleotide (s), in some embodiments. However, the oligonucleotide probe is not a replication or amplification primer as described herein. The oligonucleotide probe binds to a region that is 3' of the binding site of a primer, or, where amplification is desired, is flanked by the sequences to which the amplification primers bind, or is 3' of the binding site of a primer.

In the practice of the methods described herein, the labeled oligonucleotide probe must be first annealed to a complementary nucleic acid before the nucleic acid polymerase encounters this duplex region, thereby permitting the 5' to 3' nuclease activity to cleave and release labeled detection molecules. To enhance the likelihood that the labeled oligonucleotide probe will have annealed to a complementary target nucleic acid before primer extension polymerization reaches this duplex region, or before the polymerase attaches to the upstream oligonucleotide primer in a polymerization-independent process, a variety of techniques can be employed.

For the polymerization-dependent process, one can position the labeled oligonucleotide probe so that the 5'-end of the labeled oligonucleotide probe is relatively far from the 3'-end of the upstream oligonucleotide primer, thereby giving the probe more time to anneal before extension of the primer blocks the probe binding site. Short primer molecules generally require lower temperatures to form sufficiently stable hybrid complexes with the target nucleic acid. Therefore, the labeled oligonucleotide probe can be designed to be longer than the upstream primer, so that the labeled oligonucleotide anneals preferentially to the target at higher temperatures relative to primer annealing.

One can also use primers and labeled oligonucleotide probes having differential thermal stability. For example, the nucleotide composition of the labeled oligonucleotide probe can be chosen to have greater G/C content and, consequently, greater thermal stability than the upstream primer, in some embodiments. In other embodiments, modified nucleotides can be incorporated into the labeled oligonucleotide probe, where the modified nucleotides contain base analogs that form more stable base pairs than the bases that are typically present in naturally occurring nucleic acids.

Modifications of the labeled oligonucleotide probe that can facilitate probe binding prior to primer binding, to maximize the efficiency of the methods described herein, include the incorporation of positively charged or neutral phosphodiester linkages in the labeled oligonucleotide probe to decrease the repulsion of the polyanionic backbones of the probe and target (see Letsinger et al., 1988, J. Amer. Chem. Soc: 110: 4470); the incorporation of alkylated or halogenated bases, such as 5-bromouridine, in the probe to increase base stacking; the incorporation of ribonucleotides into the probe to force the probe:target duplex into an "A" structure, which has increased base stacking; and the substitution of 2,6-diaminopurine (amino adenosine) for some, or all of the adenosines in the probe. In preparing such modified labeled oligonucleotide probes, one should recognize that the rate limiting step of duplex formation is "nucleation," the formation of a single base pair, and therefore, altering the biophysical characteristic of a portion of the probe, for instance, only the 3' or 5' terminal portion, can suffice to achieve the desired result. In addition, because the 3' terminal portion of the probe (e.g., the 3' terminal 8 to 12 nucleotides) dissociates following exonuclease degradation of the 5' terminus by the polymerase, modifications of the 3' terminus can be made without concern about interference with polymerase/nuclease activity.

The thermocycling parameters can also be varied, in some embodiments, to take advantage of the differential thermal stability of the labeled oligonucleotide probe and upstream primer. For example, following the denaturation step in thermocycling, an intermediate temperature can be introduced which is permissible for labeled oligonucleotide probe binding but not primer binding, and then the temperature is further reduced to permit primer annealing and extension.

To favor binding of the labeled oligonucleotide probe before the upstream primer, a high molar excess of labeled oligonucleotide probe to upstream primer concentration can also be used, in some embodiments. In this embodiment, labeled oligonucleotide probe concentrations are typically in the range of about 2 to 20 times higher than the respective upstream primer concentration, which is generally 0.5-5× $10^{-7}$ M. Those of skill recognize that oligonucleotide concentration, length, and base composition are each important factors that affect the $T_m$ of any particular oligonucleotide in a reaction mixture. Each of these factors can be manipulated to create a thermodynamic bias to favor labeled oligonucleotide probe annealing over primer annealing.

In preferred embodiments, the oligonucleotide probes contain one or more mismatched nucleotides at the 5' end of the molecule, termed herein as a "5' overhang sequence." Thus, a probe can have at least one mismatch at the 5' end, but can also have two, three, four, five, six, seven, eight, nine, ten, or more mismatched nucleotides. As used herein, a "mismatched nucleotide" or a "mismatch" refers to a nucleotide that is not complementary to the target sequence at that position.

An oligonucleotide probe for use in the methods described herein is labeled with at least one detectable moiety. The detectable moiety is preferably at the 5' end of the probe, preferably 5' to the 1 or more mismatched nucleotides at the 5' end, i.e., 5' to or within the 5' overhang sequence. In some embodiments, it can also be desirable to position a detectable moiety at an internal nucleotide, e.g., a label may be at an internal nucleotide rather than the 5' end of the probe. Where the label is on the 5' terminal nucleotide of the oligonucleotide probe, the label can be positioned either on the base, or on the backbone of the probe. In some embodiments, it can be desirable to position a 5' terminal label on the backbone, e.g., to serve as a partial "block" to exonuclease activity that targets the single-stranded substrate.

In some embodiments, it can be desirable to design an oligonucleotide probe that has a particular overhang sequence on the 5' end, i.e., a particular 5' overhang sequence of mismatched or non-complementary bases. For example, the 5' to 3' exonuclease can be preferentially active towards one or more particular sequences. Accordingly, in some embodiments, the oligonucleotide probe is designed so that the one or more mismatched nucleotides at the 5' end of the probe comprises a sequence that the 5' to 3' exonuclease activity preferentially targets. In other embodiments, an oligonucleotide probe is designed to hybridize to a region of the target nucleic acid sequence that comprises a sequence that is complementary to the particular sequence that the practitioner wishes to position at the 5' end of the probe. For example, in the presence of AT-rich sequences in the 5' complementary probe region, cleavage occurs after the approximately fourth, fifth or sixth nucleotide. However, in a GC-rich 5' complementary probe region, cleavage generally occurs after the first or second nucleotide. Alternatively, the incorporation of modified phosphodiester linkages (e.g., phosphorothioate or methylphosphonates) in the labeled probe during chemical synthesis (Noble et al., 1984, Nuc Acids Res 12:3387-3403; Iyer et al., 1990, J. Am. Chem. Soc. 112:1253-1254) can be used to prevent cleavage at a selected site. Depending on the length of the probe, the length of a 5' overhang sequence, the composition of the 5' complementary region of the probe, and the position of the label, one can design a labeled oligonucleotide probe to favor preferentially the generation of specific labeled detection molecules for use in the practice of the methods described herein.

As appreciated by one of skill in the art, probes can be evaluated for sensitivity and specificity as explained in the examples section below.

In some embodiments, it can be desirable to design oligonucleotide probes further taking into consideration the following. There are several scenarios that could generate non-specific signals in the methods comprising amplification steps described herein. For example, if the 5'-end of the oligonucleotide probe anneals or partially anneals to the 3'-end of one of the primers, e.g., the reverse primer, leaving the 3' nucleotide of the probe as a mismatch, a polymerase enzyme can potentially recognize this as a substrate and cleave the probe. The cleaved oligonucleotide probe would then have an exposed 3'-end hydroxyl group, which would allow it to serve as a primer. The probe-turned into primer in this example could be extended on the reverse primer. In the next cycle, the extended probe-turned into primer could serve as the template for the reverse primer and be copied. Thus, a generated duplex could have all the sequence generated from the probe and the reverse primer, but not the template. It can therefore be desirable to design probes that do not have this problem. This can be achieved based on sequence information; further, probes can be designed to incorporate an "abasic site" in the probe, in some embodiments.

As understood by those in the art, an abasic site lacks a base at a position in the oligonucleotide probe, i.e., the sugar residue is present at the position in the probe, but there is no base. Oligonucleotide probes having an abasic site are typically synthesized with the abasic site and are commercially available (e.g., Integrated DNA Technologies, Inc., "IDT"). An abasic site present in a probe does not prevent the probe from being cleaved, or from being extended, but it prevents the reverse primer from being extended to its end in the following cycle. The end result is that no exponential amplification of the undesired products occurs. An abasic site is typically included at an internal position of the probe. The position is selected so that it does not destabilize binding of the probe to the target nucleic acid. For example, an abasic site can be positioned in the middle third of the probe sequence. In other embodiments, the abasic site is positioned at least 3 nucleotides from the 3' end of the probe; or positioned towards the 5' end of the probe, e.g., 3 nucleotides from the 5' end.

Typically, the oligonucleotide probe is labeled with a fluorescent molecule as a label or dye. In preferred embodiments, the fluorescence label is a label that has or confers an anomalous migration property, as that term is defined herein. In further preferred embodiments, the fluorescence label is fluoresein or its derivatives, including but not limited to, FAM (5-Carboxyfluorescein). While not wishing to be bound or limited by theory, it is likely that the anomalous migration properties of labels, such as FAM, described herein relates to the strong negative charge possessed by such labels. Accordingly, in some embodiments, a label for use in the methods described herein is selected based on having a strong negative charge. It is anticipated that the migration anomaly will be more pronounced with increasing negative charge in the label.

Other examples of fluorescence labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein and derivatives, such as 5-bromomethyl fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X, LuciferYellow, IAEDANS, 7-Me$_2$N-coumarin-4-acetate, 7-OH-4-CH$_3$-coumarin-3-acetate, 7-NH$_2$-4CH$_3$-coumarin-3-acetate (AMCA), monobromobimane, pyrene trisulfonates, such as Cascade Blue, and monobromotrimethylammoniobiman. Other examples of fluorescent dyes for use as detectable labels in the methods described herein, can be found, in among other places, U.S. Pat. Nos. 5,750,409; 5,366,860; 5,231,191; 5,840,999; 5,847,162; 4,439,356; 4,481,136; 5,188,934; 5,654,442; 5,840,999; 5,750,409; 5,066,580; 5,750,409; 5,366,860; 5,231,191; 5,840,999; 5,847,162; 5,486,616; 5,569,587; 5,569,766; 5,627,027; 5,321,130; 5,410,030; 5,436,134; 5,534,416; 5,582,977; 5,658,751; 5,656,449; 5,863,753; PCT Publications WO 97/36960; 99/27020; 99/16832; European Patent EP 0 050 684; Sauer et al, 1995, J. Fluorescence 5: 247-261; Lee et al., 1992, Nucl. Acids Res. 20: 2471-2483; and Tu et al., 1998, Nucl. Acids Res. 26: 2797-2802, the contents of each of which are herein incorporated in their entireties by reference. Within the methods described herein, it is critical that mononucleotides or short oligonucleotides labeled with a fluorescent molecule exhibit anomalous migration properties upon electrophoresis.

In addition, base-linked fluorophores and quenchers are well-known in the art. They can be obtained, for example, from Life Technologies (Gaithersburg, Md.), Sigma-Genosys (The Woodlands, Tex.), Genset Corp. (La Jolla, Calif.), or Synthetic Genetics (San Diego, Calif.). In some cases, base-linked fluorophores are incorporated into probe oligonucleotides by post-synthesis modification of oligonucleotides that were synthesized with reactive groups linked to bases. The fluorophores can be attached to the 3' OH of the sugar or the base.

The literature includes references providing exhaustive lists of fluorescent and chromogenic molecules and their relevant optical properties (see, for example, Berlman, Handbook of Fluorescence Spectra of Aromatic Molecules, 2nd Edition (Academic Press, New York, 1971); Griffiths, Colour and Constitution of Organic Molecules (Academic Press, New York, 1976); Bishop, Ed., Indicators (Pergamon Press, Oxford, 1972); Haugland, Handbook of Fluorescent Probes and Research Chemicals (Molecular Probes, Eugene, 1992) Pringsheim, Fluorescence and Phosphorescence (Interscience Publishers, New York, 1949). Further, the literature provides ample guidance for derivatizing label molecules for covalent attachment via common reactive groups that can be added to an oligonucleotide (see, e.g., Haugland (supra); U.S. Pat. No. 3,996,345; and U.S. Pat. No. 4,351,760).

The oligonucleotide probe can also comprise additional components, in some embodiments. These include minor groove binding proteins and/or a modified base DNA probes with conjugated minor groove binder (MGB) groups form extremely stable duplexes with single-stranded DNA targets, allowing shorter probes to be used for hybridization based assays (e.g., U.S. Pat. No. 5,801,155). Accordingly, in some embodiments, minor groove binder groups are also included in the probe, e.g., at the 3' end of the probe. A variety of suitable minor groove binders have been described in the literature. See, for example, U.S. Pat. No. 5,801,155; Wemmer & Dervan, Current Opinion in Structural Biology 7:355-361 (1997); Walker, et al., Biopolymers 44:323-334 (1997); Zimmer & Wahnert, Prog. Biophys. Molec. Bio. 47:31-112 (1986); and Reddy, et al., Pharmacol. Therap. 84:1-111 (1999). Suitable methods for attaching MGBs (as well as other moieties) through linkers to oligonucleotides are described in, for example, U.S. Pat. Nos. 5,512,677; 5,419,966; 5,696,251; 5,585,481; 5,942,610 and 5,736,626.

Nucleic Acid Polymerases

"Nucleic acid polymerases," as used herein, refer to a broad class of enzymes that catalyze the polymerization of individual nucleotides, e.g., deoxyribonucleotides and ribonucleotides, into a nucleic acid strand or polynucleotide in a template-dependent manner. Nucleic acid polymerases generally useful in the invention include DNA polymerases, RNA polymerases, reverse transcriptases, and mutant or altered forms of any of the foregoing, and have 5' to 3' exonuclease activity. In some embodiments of the aspects described herein, the enzyme having polymerase activity and/or 5' to 3' exonuclease activity can comprise a hybrid protein. The term "hybrid protein" is used herein to describe a protein that comprises amino acid residues from more than one parent sequences. Examples of hybrid polymerase proteins and methods of generating hybrid proteins are disclosed in WO2004011605, the contents of which are herein incorporated in their entirety by reference. Such polymerases are therefore non-naturally occurring variants of polymerases.

At least five families of DNA-dependent naturally occurring DNA polymerases are known, although most fall into families A, B and C. There is little or no structural or sequence similarity among the various families. As used herein, a "DNA polymerase" refers to any naturally occurring or recombinant enzyme that catalyzes the polymerization of deoxyribonucleotides into a polynucleotide DNA strand in a template-dependent manner. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In $E.\ coli$, three types of DNA polymerases have been found, DNA polymerases I (family A), II (family B), and III (family C). In eukaryotic cells, three different family B polymerases, DNA polymerases, α, δ, and ε, are implicated in nuclear replication, and a family A polymerase, polymerase γ, is used for mitochondrial DNA replication. Other types of DNA polymerases include phage polymerases.

Endogenous or naturally occurring DNA polymerases are critical for DNA replication, in which the polymerase reads an intact DNA strand as a template, and uses it as template to synthesize the new strand. The newly polymerized molecule is complementary to the template strand, and identical to the template's original partner strand. DNA polymerases can add free nucleotides only to the 3' end of the newly-forming strand, to a preexisting 3'-OH group. Therefore, DNA polymerases require a primer, as the term is defined herein, to provide a 3'-OH end at which it can add a first nucleotide. This polymerase activity results in elongation of the new strand in a 5'-3' direction. No known DNA polymerase is able to synthesize a new chain de novo.

Nucleic acid polymerases for use in the methods described herein are preferably thermostable. Among the advantages conferred by the thermostability of certain polymerases, such as Taq ($Thermus\ aquaticus$) DNA polymerase, is the ability to withstand the repeated heating and cooling inherent to PCR reactions, and to synthesize nucleic acid strands at high temperatures. Such high temperatures prevent or do not permit hybridization of mismatched primers, and do not permit or reduce formation of regions of local secondary structure, thus increasing the efficiency and success of the synthesis.

In addition to having thermostability, it is preferred that DNA polymerases for use in the methods described herein possess 5' to 3' nuclease activity or N-terminal deletion activity. In some embodiments, the polymerase that provides elongation or polymerization activity also comprises 5' to 3' exonuclease activity. In other embodiments, a separate enzyme having 5' to 3' exonuclease activity is used with a DNA polymerase enzyme having only elongation or polymerization activity. As used herein, "5' to 3' nuclease activity" refers to the ability or property of a polymerase to degrade nucleic acids in the same direction as DNA synthesis, i.e., in the 5' to 3' direction. During DNA replication, if a polymerase having 5' to 3' nuclease activity detects a fragment or nucleic acid, such as a primer or probe, annealed or hybridized to the target nucleic acid sequence that it is replicating, i.e., a double-stranded nucleic acid, the 5' to 3' nuclease activity will degrade or remove the annealed nucleic acid fragment, thereby permitting 5' to 3' synthesis to continue. It is preferred that enzymes having 5' to 3' exonuclease activity for use in the methods described herein are thermostable. In the methods described herein, the 5' to 3' nuclease activity of a polymerase removes at least 1, at least 2, at least 3, at least 4, at least 5, at least 6, at least 7, at least 8, at least 9, at least 10, or more, nucleotides of a labeled probe sequence, thereby producing a labeled detection molecule, as the term is defined herein.

It is preferred that DNA polymerases for use in the methods described herein have low error rates or high fidelity. As used herein, the "error rate" of a DNA polymerase refers to the number of incorrect, i.e., non-complementary base pairs, a DNA polymerase adds to a sequence being synthesized per 10000 nucleotides added per replication cycle. For example, the error rate of Taq polymerase was initially estimated at $2 \times 10^{-4}$ nucleotides/cycle (Saiki et al., 1988). Typically, polymerases with 3' to 5' exonuclease activity have low error rates, but can sometimes have decreased yields. Accordingly, in some embodiments, a polymerase for use in the methods described herein has 3' to 5' exonuclease activity. In other embodiments, the polymerase has no 3' to 5' exonuclease activity.

Some polymerases, such as Taq DNA polymerase, have a property for adding nontemplated nucleotides to the 3' ends of a synthesized DNA molecule. Accordingly, in some embodiments, a polymerase for use in the methods described herein does not add non-templated nucleotides to the 3' end of a synthesized DNA molecule.

DNA polymerases and their properties are described in detail in, among other places, DNA Replication 2nd edition, Kornberg and Baker, W.H. Freeman, New York, N.Y. (1991). Known conventional DNA polymerases useful in the invention include, but are not limited to, *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermus aquaticus* (Taq) DNA polymerase (Chien et al., 1976, J. Bacteoriol, 127: 1550), *Thermus flavus* (Tfl) polymerase (Kaledin, A. S. et al. (1981) Biokhimiia 46, 1576-84), and *E. coli* DNA polymerase I (Lecomte and Doubleday, 1983, Polynucleotides Res. 11:7505). In addition, any mutants, variants, or fragments maintaining polymerase activity, thermostability, and 5' to 3' exonuclease activity are also contemplated for use in the methods described herein.

A non-limiting list of DNA polymerases for use in the methods described herein is provided in Table 1.

TABLE 1

Exemplary DNA Polymerases

| DNA polymerase | | | | | |
|---|---|---|---|---|---|
| Generic name | Trade name | Biological source | Supplier | Product ends | Exonuclease activity |
| Taq (native and/or recombinant) | — | *Thermus aquaticus* | Ambion, Amersham Pharmacia Biotech, Boehringer Mannheim, Clontech, Fisher, Life Technologies, Marsh Biomedical, Perkin Elmer, Promega, Qiagen, Sigma, Stratagene | 3'A | 5'-3' |
| Tbr | DyNAzyme | *Thermus brocianus* | MJ Research | —a | 5'-3' |
| Tfl | | *Thermus flavus* | Promega, Epicentre Technologies | Blunt | 5'-3' |
| Tth | — | *Thermus thermophilus* | Amersham Pharmacia Biotech, Boehringer Mannheim, Epicentre Technologies, Perkin Elmer, Promega | 3' A | 5'-3' |

In some aspects of the methods described herein, the sample comprising a target nucleic acid is generated from an RNA template, and reverse transcriptases can be used. Reverse transcriptases are DNA polymerase enzymes that transcribe single-stranded RNA into double-stranded DNA. Reverse transcriptase enzymes typically include an RNA-dependent DNA polymerase and a DNA-dependent DNA polymerase, which work together to perform transcription. Reverse transcriptases can thus also help in the formation of a double helix DNA, once RNA has been reverse transcribed into a single strand complementary DNA (cDNA). Reverse transcriptases that can be useful in the methods described herein include, but are not limited to, reverse transcriptases from HIV, HTLV-1, HTLV-II, FeLV, My, SIV, AMV, MMTV, MoMuLV and other retroviruses (see Levin, Cell 88:5-8 (1997); Verma, Biochim Biophys Acta. 473:1-38 (1977); Wu et al., CRC Crit. Rev Biochem. 3:289-347 (1975)).

Nucleic Acid Replication and Amplification

The methods described herein relate to the exploitation of anomalous migration properties during electrophoresis of labeled detection molecules, released by the 5' to 3' exonuclease activity of polymerases on a hybridized duplex composed of a labeled oligonucleotide probe and a target nucleic acid, to detect and measure target nucleic acid sequences of interest. The methods described herein are an improvement over current detection methods, as the anomalous migration properties of labeled detection molecules in electrophoretic systems provide a novel means of discriminating one or more target nucleic acid sequences using the same label. In other words, using a single fluorescent label, such as FAM, nucleic acid sequences of different lengths can be discriminated based on a combination of both a fluorescence signal and a migration property. Thus, the methods described herein increase the number of target species that can be detected using a single label. These methods are especially suited for use in conjunction with a PCR-based amplification method or system, as described herein.

In some aspects of these methods, target nucleic acid species to be detected using the approaches described herein are first amplified. The most common procedure for DNA amplification, the polymerase chain reaction (PCR) technique, is disclosed in U.S. Pat. Nos. 4,683,202; 4,683,195; 4,800,159; and 4,965,188. The PCR method is also described in Saiki et al., 1985, Science 230:1350. PCR can be used in any of a variety of applications requiring or aided by amplification of nucleic acids including, but not limited to, direct cloning from genomic DNA or cDNA, in vitro mutagenesis and engineering of DNA, genetic fingerprinting of forensic samples, assays for the presence of infectious agents, prenatal diagnosis of genetic diseases, analysis of allelic sequence variations, analysis of RNA transcript structure, genomic footprinting, and direct nucleotide sequencing of genomic DNA and cDNA.

Accordingly, "polymerase chain reaction" or "PCR" refers to an in vitro method for enzymatic synthesis of specific nucleic acid sequences that uses two oligonucleotide primers that hybridize to opposite strands and flank the region of interest in the target nucleic acid sequence. A repetitive series of reaction steps involving template denaturation, primer annealing, and the extension of the annealed primers by a DNA polymerase results in the exponential accumulation of a specific target nucleic acid fragment, the termini of which are defined by the 5' ends of the oligonucleotide primers. PCR is capable of producing a selective enrichment of a specific DNA sequence by a factor of at least $10^9$.

In a typical PCR protocol, a nucleic acid sample having a target nucleic acid sequence to be amplified is denatured by heating the sample. In the presence of a nucleic acid polymerase and excess nucleoside triphosphates, oligonucleotide primers that hybridize specifically to the target sequence can prime new nucleic acid synthesis. The first cycle of PCR is characterized by a product of indeterminate length; however, the subsequent cycle onwards produces a discrete "short product," i.e., a target nucleic acid species, which accumulates exponentially with each successive round of amplification.

Generally, oligonucleotide primers are added in vast excess compared to the nucleic acid to be amplified. Under the appropriate conditions, oligonucleotide primers hybridize to opposite strands of a double-stranded nucleic acid sequence and are oriented with their 3' ends facing each other on each strand, so that synthesis by a nucleic acid polymerase that catalyzes growth of new strands in the 5' to 3' direction extends across the segment of nucleic acid between them. For the methods described herein, the nucleic acid polymerase used also has or is associated with a 5' to 3' nuclease activity.

One round of synthesis results in new strands of indeterminate length which, like the parental strands, can hybridize to the primers upon denaturation and annealing. These products accumulate only arithmetically with each subsequent cycle of denaturation, annealing to primers, and synthesis. However, the second cycle of denaturation, annealing, and synthesis produces two single-stranded products that together compose a discrete double-stranded product that is exactly the length between the primer ends. Each strand of this discrete product is complementary to one of the two primers and can therefore participate as a template in subsequent cycles. The amount of this product doubles with every subsequent cycle of synthesis, denaturation, and annealing, accumulating exponentially so that 30 cycles should result in a $2^{28}$-fold (270 million-fold) amplification of the target nucleic acid product.

A typical PCR amplification cycle comprises three steps, "denaturation," "annealing" or "hybridizing," and "extension." As used herein, "denaturation" or "nucleic acid melting" refers to the separation or unwinding of double-stranded nucleic acids and separation into single-stranded strands through the breaking of hydrogen bonding between complementary bases. Both terms are used herein to refer to the process as it occurs when a mixture is heated to a specific temperature, although "denaturation" can refer to the separation of nucleic acid strands induced by chemicals like urea. It is critical that complete strand separation occur during the denaturation step. Higher temperatures required for complete denaturation are associated with high GC content in the nucleic acids. A typical temperature for the denaturing step in a typical PCR cycle is at least 92° C., at least 93° C., at least 94° C., at least 95° C., at least 96° C., at least 97° C., at least 98° C., at least 99° C., or higher. The duration of the denaturing step in a typical PCR cycle is approximately 30 seconds.

The "annealing" or "hybridization" step of a PCR cycle refers to the step wherein the primers and/or probes stably anneal to the template. Primers with relatively low GC content (<50%) can require temperatures lower than 55° C. for full annealing. On the other hand, this can also increase the quantity of nonspecific products. For primers with high GC content, higher annealing temperatures can be necessary. Methods for optimization of primer annealing are known to one of skill in the art. As with denaturation, the time for this step is based mainly on the time it takes to reach the proper temperature, because the primers are in such excess that the annealing reaction occurs very quickly. (Note, however, the earlier discussion regarding ways to bias probe binding over primer binding for the methods described herein.)

The "extension" step of a PCR cycle refers to the step where the polymerase activity of a polymerase adds nucleic acids to the 3'-OH of an annealed primer, thereby generating a complementary strand to the template nucleic acid. The extension temperature is chosen to be close to the optimal temperature of the polymerase being used, but is also chosen to be one at which the primers are prevented from dissociating. For example, 72° C. is close to the optimal temperature for Taq DNA polymerase (~75° C.), but is a low enough temperature to prevent annealed primers from dissociating from the nucleic acid template. Indeed, when Taq DNA polymerase is used, primer extension typically can begin during annealing, because Taq DNA polymerase is partially active at 55° C. and even lower temperatures (Gelfand, 1989). The duration of the extension step depends mainly on the length of the sequence to be amplified. Typically, a duration of 1 min per kb of target nucleic acid product length is sufficient. In some embodiments, a series of PCR cycles can end with a final and separate extension step that is longer, for example, 5-10 minutes to ensure completion of target nucleic acid product synthesis.

In some aspects of the methods described herein, a starting sample can be an RNA sample. In planning amplification of a sample comprising RNA or an RNA target nucleic acid, factors that can be considered include, but are not limited to: (1) method of preparation of the template RNA; (2) design of the specific oligonucleotide primers; (3) enzymatic synthesis of the first strand of cDNA using the appropriate primer; and (4) enzymatic amplification.

Depending upon available quantities, total RNA, cytoplasmic RNA, or poly(A)+ RNA can be used as the starting sample for use in the methods described herein. In some embodiments, a starting sample can comprise a crude cellular preparation, such as a cellular or tissue extract.

In some aspects, the methods described herein provide novel means of performing quantitative PCR (q-PCR) for high-throughput analysis of RNA expression. The high-throughput designs described herein in some aspects allow analysis of the levels of transcripts from a number of target sequences of interest, such as specific gene sequences, at one time, by using the appropriate primer set and labeled oligonucleotide probe for each target sequence of interest. In some embodiments, the quantification of a nucleic sequence of interest can be an "absolute quantification," while in other embodiments, the quantification can be a "relative quantification." As used herein, "absolute quantification" means that the absolute copy number of a target sequence of interest is measured and determined. As used herein, "relative quantification" means that a quantitative difference in copy number between two samples, e.g., experimental and control, is measured by normalizing both samples to an endogenous reference.

Electrophoretic Separation Methods

Detection or verification of the labeled detection molecules and other reaction products, such as amplified target nucleic acid sequences, can be accomplished by a variety of methods and can be dependent on the label(s) employed. In the aspects described herein, the reaction products, including the labeled detection molecules, are subjected to size analysis methods. Size separation of nucleic acids is well known, e.g., by agars or polyacrylamide electrophoresis or by column chromatography, including HPLC separation. A preferred approach for the aspects described herein uses capillary electrophoresis, which is both rapid and accurate, readily achieving separation of molecules differing in size by as little as one nucleotide. Capillary electrophoresis uses small amounts of sample and is well-adapted for additional detection by, for example, fluorescence detection.

Nucleic acid fragments, such as DNA fragments, have traditionally been separated and analyzed by electrophoretic methods, such as slab gel electrophoresis. Such electrophoretic techniques separate nucleic acid species based upon their size and ionic properties. An ion (i) placed in an electric field will move in the direction parallel to the field towards the oppositely charged electrode with a velocity ($v_1$) defined as follows:

$$v_i = \mu_i E = \mu_i V/L$$

where $\mu_i$ is the mobility of the ion, E is the electric field in volts per centimeter, V is the voltage along or across the column, and L is the total column length. The electrophoretic mobility of a given ion ($m_i$) is equal to:

$$m_i = q_i/6\pi\eta a_i$$

where $q_i$ is the charge on the ion, $\eta$ is the viscosity of the buffer or gel matrix, and $a_i$ is the radius of the ion.

In the case of slab gel electrophoretic methods, voltage applied at the ends of a gel, such as an agarose gel, generates an electric field with a strength defined by the length of the gel and the potential difference at the ends (V/cm). Nucleic acid molecules exposed to this electric field migrate toward the anode due to the negatively charged phosphates along the nucleic acid backbone. The migration velocity is limited by the frictional force imposed by the gel matrix. While charge and/or size can affect the rate at which macromolecules will pass through a gel, the charge to mass ratio is the same for DNA molecules of different lengths. It is the size of the DNA, therefore, that determines the rate at which it passes through the gel, thereby allowing an effective separation of DNA fragment-length mixtures by electrophoresis (This, of course, does not take into account the effect of appended moieties, such as fluorescent labels, on migration). Such gel matrices are usually either polyacrylamide or agarose, and separations can be achieved in the presence (e.g., for ssDNA) or the absence (e.g., for dsDNA) of dissociating agents, such as urea or formamide. Such slab gel systems can analyze multiple samples in the same separation (i.e., gel(s)) at low cost, but normally take several hours to complete. The nucleic acid fragments or DNA are typically visualized with stains, UV shadowing, intercalating dyes, such as ethidium bromide, and sometimes radioactive labels.

Capillary electrophoresis (CE) is a very powerful electrophoretic method for the separation of nucleic acid fragments. CE can be performed by methods well known in the art, for example, as disclosed in U.S. Pat. Nos. 6,217,731; 6,001,230; and 5,963,456, the contents of each of which are herein incorporated in their entireties by reference. CE offers a number of advantages over slab gel separations in terms of speed, resolution, sensitivity, and data handling. This is, in part, because the CE separation occurs inside a small-diameter (50- to 100-μm), typically quartz, capillary in the presence of high (kilovolt-level) separating voltages. Separation times are generally only a few minutes. The nucleic acid fragments can be detected, for example, by UV absorption or by fluorescent labeling, both of which eliminate the need to use mutagenic substances (e.g., ethidium bromide) or dispose of radioactive waste. The quantity of DNA required for the separation is in the nanogram range. Single-base resolution can be readily obtained on fragments up to several hundred base pairs in size. In the presence of appropriate standards, fragments can be accurately sized, based on relative electrophoretic mobility.

CE has found increasing use in a number of analytical applications where nucleic acid separations are required. These include, but are not limited to, assessment of the purity of synthetic oligonucleotides and their modifications, analysis of PCR products, sequencing of fluorescent DNA, analysis of restriction maps, accurate sizing of restriction fragments for genetic analysis, forensic analysis of biological samples, genotyping, and analysis of conformational polymorphisms. Multicapillary automated DNA sequencing instruments using laser fluorescence detection systems based on CE have also been developed, and are commercially available.

The separation of nucleic acid fragments by CE occurs within the walls of a capillary, such as a fused-silica capillary. Since the negatively charged nature of this surface has a dramatic impact on the resolution achieved during the separations, the vast majority of CE separations are done in "coated" capillaries whose surface has been modified to be chemically inert to nucleic acids. The capillaries are filled with a sieving matrix, and nucleic acid fragments are separated on the basis of size, analogously to slab gel separations. The sieving matrix can be a chemically cross-linked gel (static gel), such as polyacrylamide, or a flowable (non-cross-linked) polymer, such as modified cellulose or non-cross-linked polyacrylamide. Single-stranded DNA (ssDNA) fragments as small as 5 bases can be readily separated with single-base resolution. Fragments of double-stranded DNA (dsDNA) as large as 20 kb are also separated, although not with single-base-pair resolution.

The selection of the appropriate matrix can significantly affect the quality of the separation. The general rule for matrix selection is that the larger the DNA fragment, the weaker the sieving capabilities of the matrix. With either a cross-linked or non-cross-linked gel in the capillary, the matrix offers a frictional resistance to the movement of the DNA through the gel medium that is proportional to the size of the species. The frictional resistance can vary with the molecular weight, concentration, and chemical composition of the flowable gel polymer or the pore size in the cross-linked gel, and must be optimized for the particular size of the DNA to be separated. A detailed description of the theory of DNA motility in entangled polymer solutions can be found in Grossman (1991).

Cross-linked polyacrylamide is best used for the separation of synthetic oligonucleotides—both native and modified versions. However, flowable polymers can also be used for oligonucleotide analysis and for the separations of automated sequencing ladders. Where dsDNA fragment analysis is required, flowable polymers are routinely used. For the methods described herein, it is important to keep in mind that the labeled detection molecules are single-stranded and short, generally on the order of 0 (dye only), to 6, 7, 8, 9, or 10 nucleotides; however it is also important to keep in mind that the anomalous migration patterns tend to make them migrate as larger species, e.g., on the order of 95-100 nucleotides for FAM-labeled mononucleotides.

As used herein, "cross-linked gels" refer to fixed gels, such as polyacrylamide gel, that are polymerized inside the capillary, usually covalently bound to the capillary surface, and are not removed from the capillary between runs. Such cross-linked gels can be reused for 30 to 100 separations before losing resolution. The capillary is then discarded, since the polyacrylamide gel cannot be regenerated.

Flowable polymers have the advantage of wide fragment-separation ranges. A "flowable polymer" or "flowable polymer matrix" refers to viscous hydrophilic polymer solutions that can be pumped into a capillary, such as, but not limited to, hydroxypropyl methyl cellulose (HPMC), hydroxyethylcellulose (HEC), polyethylene oxide (PEO), or non-cross-linked linear polyacrylamide. In some embodiments, the same flowable polymer matrix can be used repeatedly when small molecules, such as synthetic oligonucleotides are being analyzed. Alternatively, the polymer can be used once, discarded, and replaced with fresh matrix prior to the next sample. This latter embodiment is preferred where larger DNA molecules are present in the samples—e.g., for fragment analysis and DNA sequencing analysis. A flowable polymer can be expelled from the capillary by pressure at the end of each electrophoretic separation; fresh matrix is then reloaded into the capillary prior to the next separation.

Usually, a coated capillary is utilized to eliminate the charge effects that are contributed by the native silica surface. With cellulose-derived polymers or some specially modified acrylamides, however, uncoated capillaries may be used, because of the strong interaction of the polymer with the inner surface of the bare fused-silica capillary, in essence forming its own coating.

Separation buffers for use in capillary electrophoretic methods are frequently variants of Tris/borate/EDTA (TBE) mixtures and are buffered at alkaline pH. Urea (e.g., 6 to 8 M) is often included in the buffer, as a denaturant, that keeps the DNA in single-stranded conformation when required, such as when analyzing ssDNA (e.g., synthetic oligonucleotides). Urea can be omitted from the buffer for analyses where secondary structure plays an important role in the separation, e.g., single-nucleotide polymorphisms or conformational polymorphisms. Samples are loaded onto the capillary by electrokinetic, or pressure, injection. Separation times range from 10 to 45 min, at voltages between 1 and 10 kV.

CE separation in its simplest form can be achieved by passing a high voltage between two buffer reservoirs that are joined by a fused silica capillary filled with liquid or gel. This results in an electric field that drives the nucleic acid molecules of interest from one end of the capillary to the other. The capillaries are preferably 20 to 80 cm long and 50 to 100 µm in internal diameter, with total volumes in the 1- to 2-µl range. The combination of high field strength and large surface-area-to-volume ratio of the capillaries results in rapid and very efficient separations of, for example, both ssDNA and dsDNA. Sample loading can be accomplished from as little as 1 µl, with starting sample concentrations of ~1 µg/ml for UV detection and ~1 pg/ml or less for laser-induced fluorescence detection. The capillaries are preferably thin walled, which allows for dissipation of the Joule heating resulting from the high voltages (10 to 30 kV) that are necessary for high-performance electrophoretic separations. The fused-silica capillary can be coated on the outside with a polyimide layer that eliminates oxidation of the fused-silica glass and confers tensile strength to the capillary. The polyimide sheathing can be carefully removed from a small portion of the capillary to expose a section of the silica. This clear section of the capillary can be inserted into the light path of a UV or fluorescence detector, and becomes an "on-column flow cell." As the nucleic acid molecules migrate through the capillary as a result of the electric field, they pass through the detector light path and are measured by UV or fluorescence detection.

In preferred embodiments of the aspects described herein, a CE instrument for use with the methods of detecting nucleic acid molecules comprises a suitable sample injection module and a detector module, and can further comprise additional modules, such as temperature control modules, etc.

High-throughput CE apparatuses are available commercially, for example, the HTS9610 High throughput analysis system and SCE 9610 fully automated 96-capillary electrophoresis genetic analysis system from Spectrumedix Corporation (State College, Pa.); P/ACE™ 5000 series and CEQ series from Beckman Instruments Inc (Fullerton, Calif.); and ABI PRISM 3100, 3130, 3130xL, 3500, 3500xL, 3730, and 3730xL genetic analyzers (Applied Biosystems, Foster City, Calif.). Near the end of the CE column, in these devices the nucleic acid fragments pass a fluorescence detector which measures signals of fluorescent labels. Accordingly, these apparatuses provide automated high-throughput for the detection of labeled detection molecules having anomalous migration properties, as described herein.

In some embodiments of the methods described herein, matrix-embedded microfluidic separation methods and matrix-embedded microfluidic devices and systems that can detect labeled detection molecules are contemplated for use with the methods described herein. Microfluidic systems can provide fluid handling and amplification technologies that can be applied to the methods described herein. In some such embodiments, samples are drawn into microfluidic devices that comprise networks of microscale cavities (channels, chambers, etc., having at least one dimension less than about 500 µM in size and often less than about 100 µM) and the samples are mixed, diluted, aliquoted or otherwise manipulated in the network of cavities (e.g., channels and/or chambers). These processes can be multiplexed by using a device that comprises multiple capillary channels, permitting many samples to be drawn into the network and processed simultaneously. Alternatively, multiple samples can be sequentially drawn into a microfluidic device and routed internally to multiple channels for simultaneous processing and analysis (see, for example, U.S. Pat. No. 6,482,364; U.S. Pat. No. 6,042,709; U.S. Pat. No. 6,287,520, and U.S. Pat. No. 6,235,471, the contents of each of which are herein incorporated by reference in their entireties.

Various chromatographic techniques of separating molecular species using a microfluidic device are described in U.S. Pat. Nos. 7,128,876, 6,702,256, and 6,958,119, which are incorporated herein by reference in their entireties.

In preferred embodiments, the nucleic acid separation region of a microfluidic device for use with the methods described herein comprises an electrophoretic separation column. In such embodiments, the electrophoretic separation column can comprise a matrix or solid phase media including, but not limited to, poly-N,N-dimethylacrylamide, methylcellulose, hydroxyethylcellulose, hydroxypropylcellulose, hydroxypropylmethylcellulose, dextran, linear polyacrylamide, poly-N-acryloylaminoethoxyethanol, polyacryloylaminopropanol, poly(acryloylaminoethoxy)ethyl-glucopyranoside, poly(ethylene glycol) (PEG), poly(ethylene oxide), poly(vinyl pyrrolidone) (PVP), agarose, polysaccharides, puronic polyols, polyether-water mixture, lyotropic polymer liquid crystals, or a mixture of one or more thereof. In some embodiments, the matrix used in the electrophoretic separation column of a microfluidic device can comprise a crosslinked polymer, an agarose gel, a polyacrylamide gel, a cross-linked polyacrylamide gel, a nondenaturing polyacrylamide gel, or a denaturing polyacrylamide gel. Any known medium or buffer used to carry out electrophoretic separation is useful in such embodiments. Examples of buffers commonly employed in such embodiments are tris-HCl, tris-acetate, tris-phosphate, tris-borate, sodium hydroxide, urea, glycine, EDTA, or mixtures of these. The buffers can be employed over a range of pH. In embodiments, the pH of the buffer solution is adjusted to about 7 to 9, about 7.5 to 8, or about 7.5 to 7.8.

Commercially available, high-throughput microfluidic systems that include features for detecting nucleic acids include, but are not limited to, the 250 HTS system and AMS 90 SE from Caliper Technologies (Mountain View, Calif.), as well as the Agilent 2100 bioanalyzer (Agilent, Palo Alto, Calif.). Additional details regarding systems that comprise detection (and separation/detection) capabilities are described in, for example, Parce et al. "High Throughput Screening Assay Systems in Microscale Fluidic Devices" WO 98/00231, the contents of which are herein incorporated by reference in their entireties.

In other embodiments of the methods described herein, microfluidic devices and systems are not used with the methods described herein, i.e., the detection of a labeled detection molecule and a target nucleic acid are not performed using a microfluidic device.

Multiplex

The method described herein can be adapted to provide analysis of two or more species (i.e., a plurality, e.g., 2, 3, 4, 5, 6, 7, 8, 9, 10, 15, 20, 25, 30, 40, 50, 75, 100, 250, 1000, or more) of target nucleic acids from a single sample by varying the length of the 5' overhang of the labeled oligonucleotide probe specific for each target nucleic acid sequence, such that each labeled detection molecule generated from each labeled oligonucleotide probe has a unique anomalous migration property. In one aspect, the relative sizes of the labeled detection molecules are distinguishable by electrophoresis or capillary electrophoresis. Accordingly, in some embodiments of the aspects described herein, multiple labeled oligonucleotide probes comprising different 5' overhang sequence lengths and/or different fluorescent labels can be used in the methods described herein to perform multiplex assays.

In some embodiments of the methods described herein, one can achieve allele-specific or species-specific discrimination using multiple labeled oligonucleotide probes in the methods, for instance, by using labeled oligonucleotide probes that have different $T_m$s and conducting the annealing/cleavage reaction at a temperature specific for only one probe/allele duplex. For instance, one can choose a primer pair that amplifies both alleles of a specific target nucleic acid sequence and use two probes, each labeled with the same label but having different 5' overhang sequence lengths, and a complementary region specific for only one allele. One can then achieve allele specific discrimination by examining the types of labeled detection molecules generated. In such an embodiment of the methods described herein, each labeled oligonucleotide probe is designed to be exactly complementary, at least in the 3' terminal region, to one allele but not to the other allele(s). With respect to the other allele(s), the probe is mismatched in the 3' terminal region of the probe, and has a different 5' overhang sequence length than the other probe so that a different labeled detection molecule is generated as compared to the labeled detection molecule generated when the other probe is hybridized to its exactly complementary allele.

EXAMPLES

The non-limiting examples presented below are intended to be illustrative of the various methods described herein.

The approaches and methods described herein are based, in part, on the elucidation of anomalous migration properties of nucleic acid molecules when conjugated to a fluorescent label. The elucidation of the anomalous migration properties permits the exploitation of those properties for quantitative detection in, for example, multiplex PCR.

Briefly, nucleic acid targets were amplified and labeled using "TaqMan™-style" probe-based assays, according to the manufacturers' instructions. Different manufacturers' reagents and assays used in the amplification reactions included Argene, ABI, Qiagen, and Propesse, as well as assays developed in-house. The amplified and labeled products were separated using capillary electrophoresis and detected via fluorescence.

Example 1

Detection of Fluorophore Labeled Non-Target Sequence Products

In the experiments described herein, the TaqMan assays comprised: primers specific for amplification of a desired target nucleic acid sequence; an oligonucleotide probe that annealed to its probe binding site within the target sequence amplified by the primers, where the oligonucleotide probe comprised a fluorophore covalently attached to its 5'-end, such as 6-carboxyfluorescein (FAM); a polymerase having 5' to 3' exonuclease activity, such as HotStar Taq polymerase or AmpliTaq Gold® DNA polymerase; and appropriate reagents for the amplification reaction, including nucleotides and buffers.

In the experiments described in FIGS. 1A-1F, the oligonucleotide probes used had complete complementarity to their probe binding sites. Accordingly, during the amplification reactions, the polymerase activity extended the primer from its 3' end, thereby synthesizing a complementary strand, while the 5' to 3' exonuclease activity of the polymerase degraded the labeled oligonucleotide probe, which had annealed downstream of the oligonucleotide primer to its binding site on the target nucleic acid sequence being amplified. Degradation of the probe released the fluorophore. In some examples, the fluorophore labeled oligonucleotide probe further comprised a quencher at the 3'-end, such as tetramethylrhodamine (TAMRA). The amplified products were then separated and detected using capillary electrophoresis and fluorescence detection. In some examples, the forward primer (i.e., the primer annealing upstream of the oligonucleotide probe), was labeled, for example, with a TYE label, as illustrated in FIG. 1A. In such examples, the amplified target sequence therefore comprised a TYE fluorescent label.

Figure 1D:
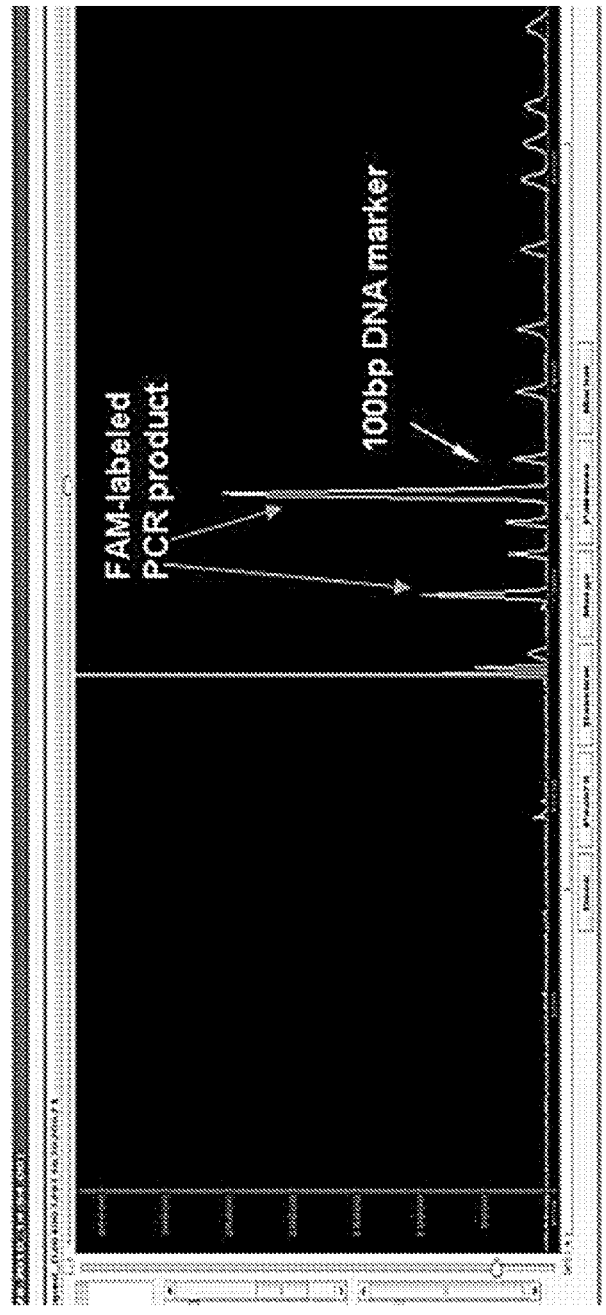
Figure 1E:
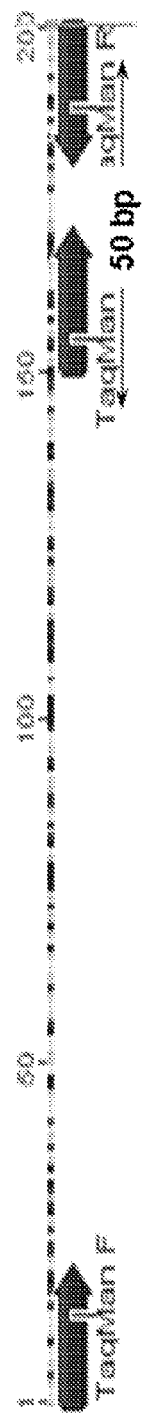
Figure 1F:
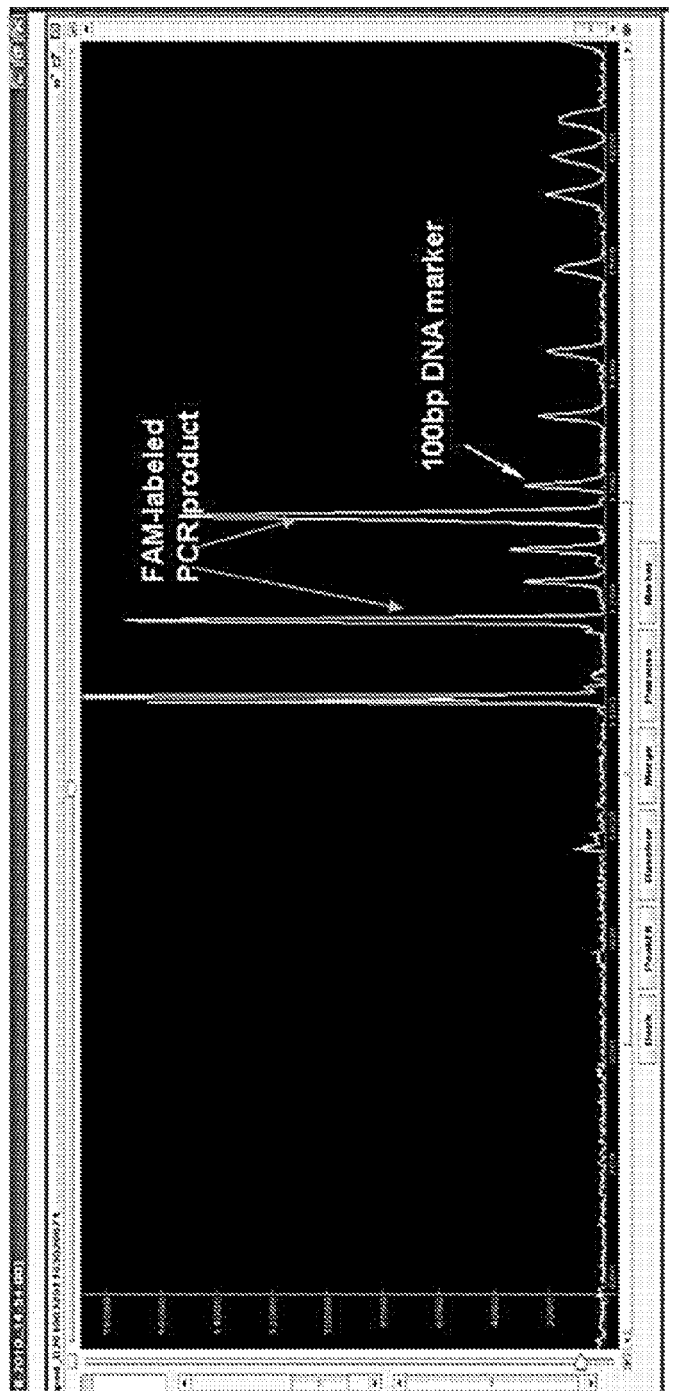
Figures 2A, 2B:
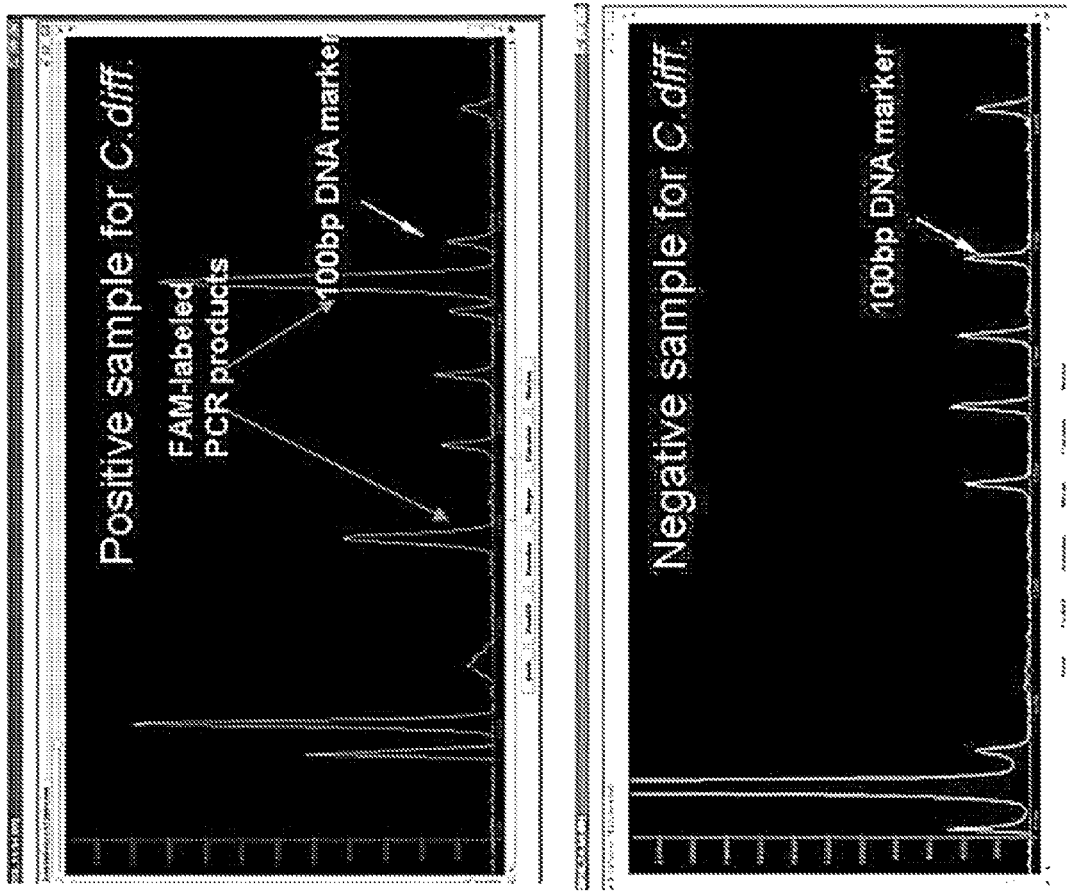
FIGS. 2A-2D demonstrate that the fluorophore-labeled products were not generated in the absence of a template or target nucleic acid species. In the absence of the templates C. diff.
Figures 2C, 2D:
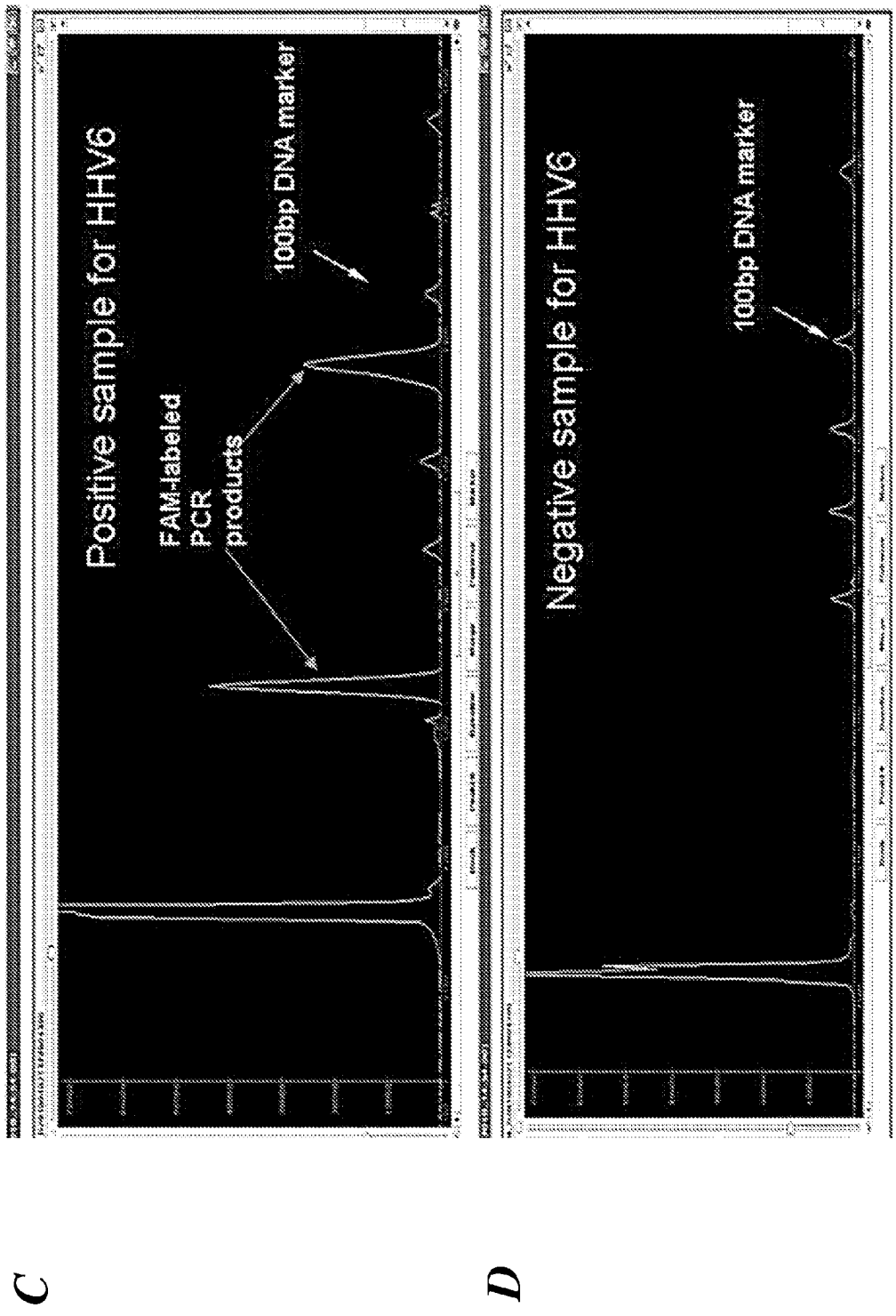

In these experiments, it was surprisingly found that all the tested TaqMan assays generated fluorophore-labeled products with approximate apparent sizes of 50 and 95 bp, regardless of the target nucleic acid sequence being amplified, in addition to the amplified target sequence (see, for example, FIG. 1B, FIG. 1D, and FIG. 1F, where the target sequences are PF4, CMV, and EBV, respectively). These products and their corresponding peaks were found to be reproducible and specific, demonstrated dose response to target concentrations, and demonstrated low copy number assay sensitivity.

Figure 3A:
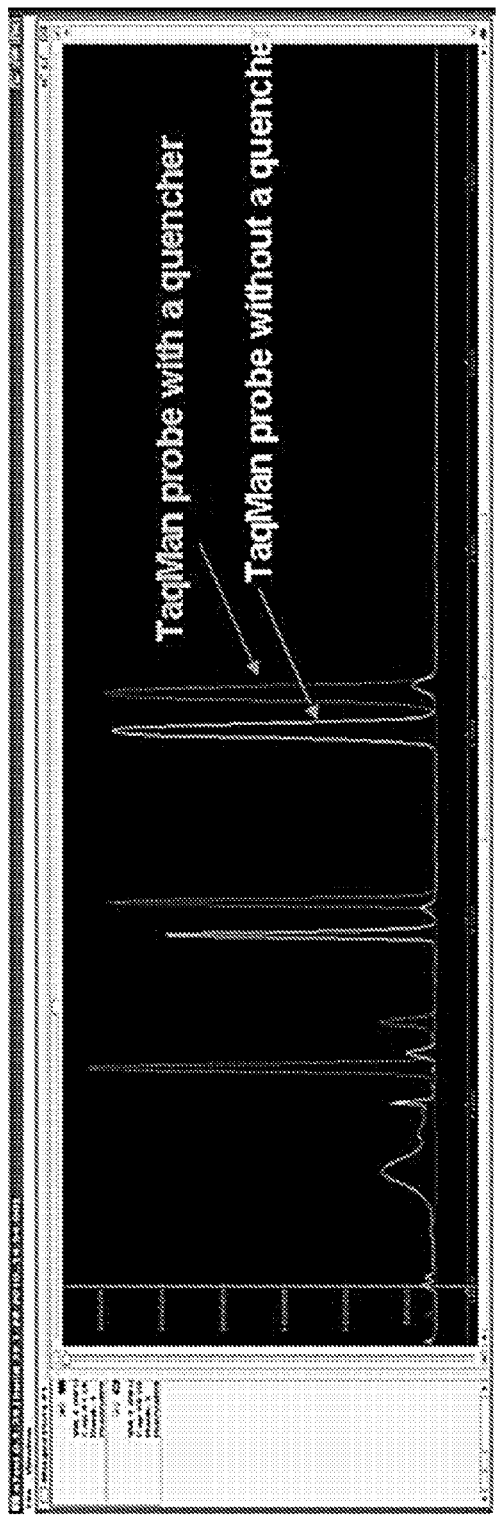
FIGS. 3A-3B demonstrate that the fluorophore-labeled products were generated whether or not the labeled oligonucleotide probe comprised a quencher molecule or not.
Figure 3B:
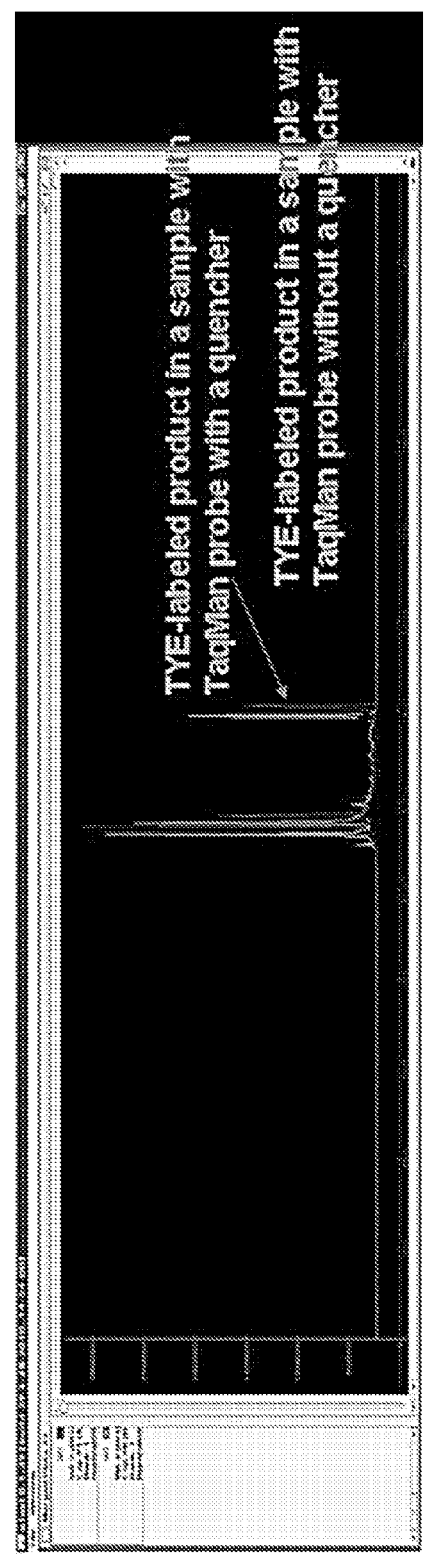

Further, it was determined that the fluorophore-labeled products were not generated in the absence of a template or target nucleic acid species, as shown in FIGS. 2A-2B and 2C-2D, where in the absence of the templates *C. diff.* and HHV6 respectively, FAM-labeled PCR products were not observed. It was also found that these fluorophore-labeled products were generated whether or not the labeled oligonucleotide probe comprised a quencher molecule or not, as demonstrated in FIGS. 3A-3B.

Example 2

Anomalous Migration Dependent on 5' to 3' Exonuclease Activity

Figure 4A:
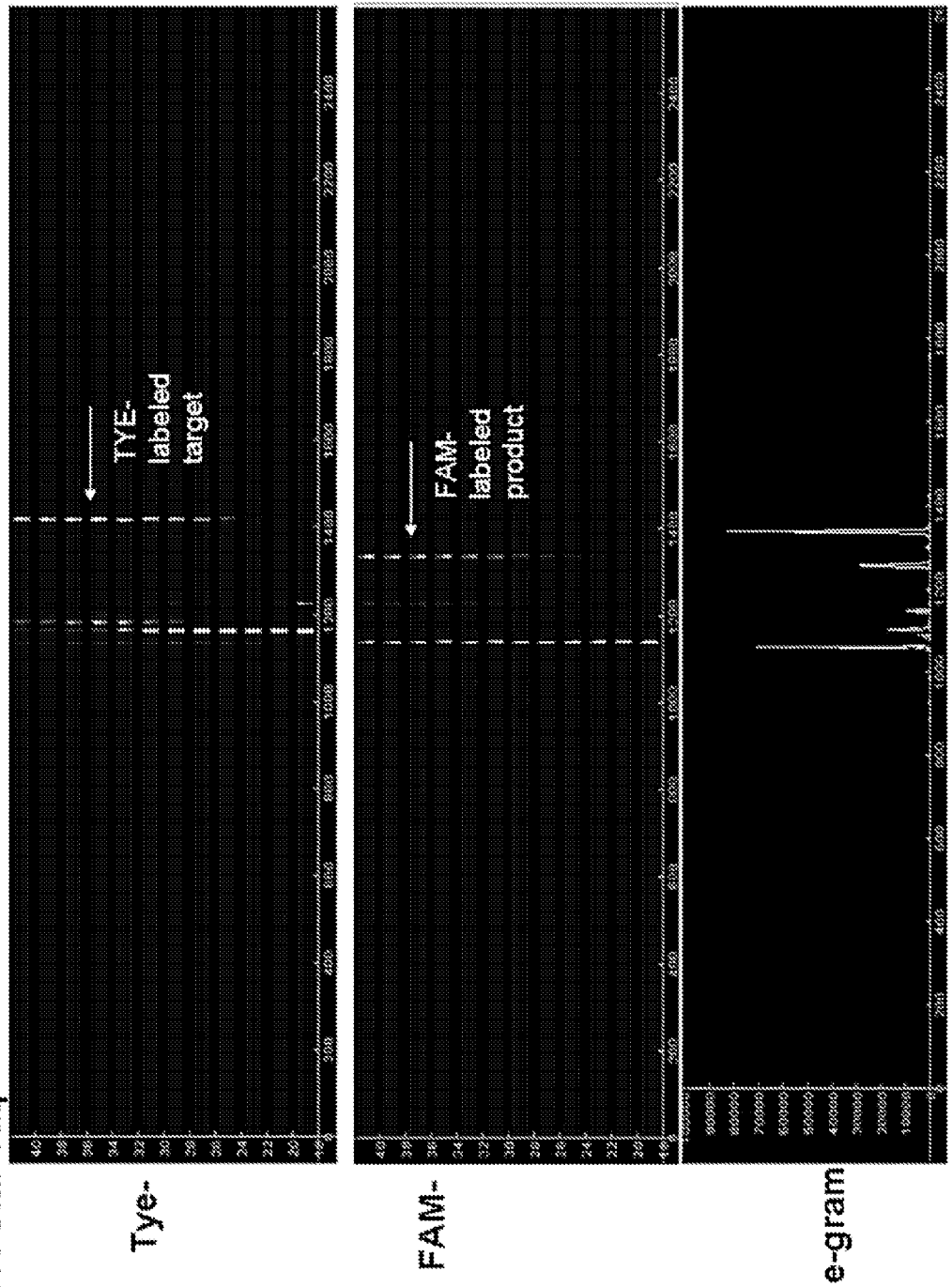
FIGS. 4A-4D demonstrate that polymerases having 5' to 3' exonuclease activity are required to generate labeled molecules having anomalous migration properties. TaqMan™-style assays utilizing different polymerase enzymes were performed.
Figure 4B:
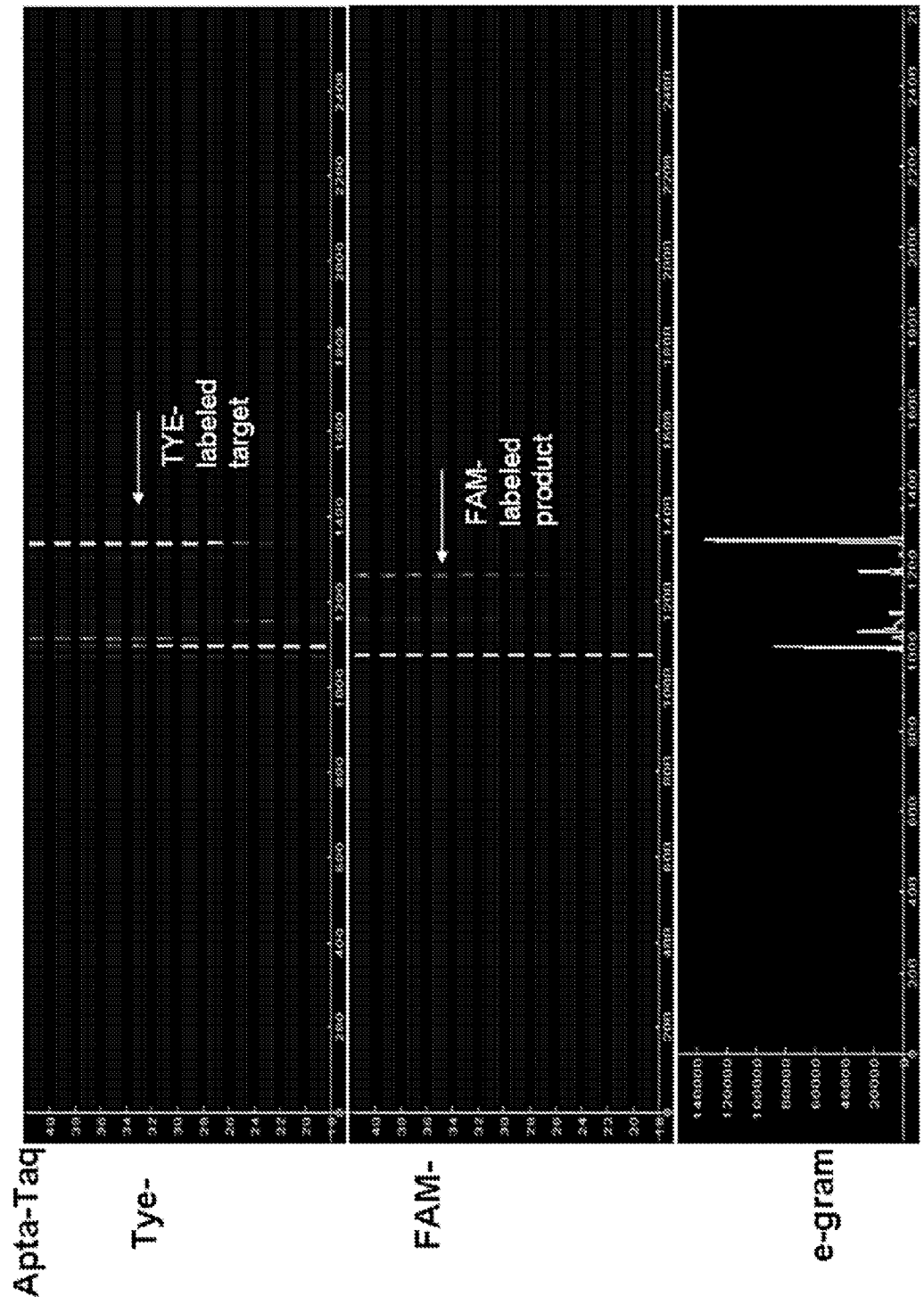
Figure 4C:
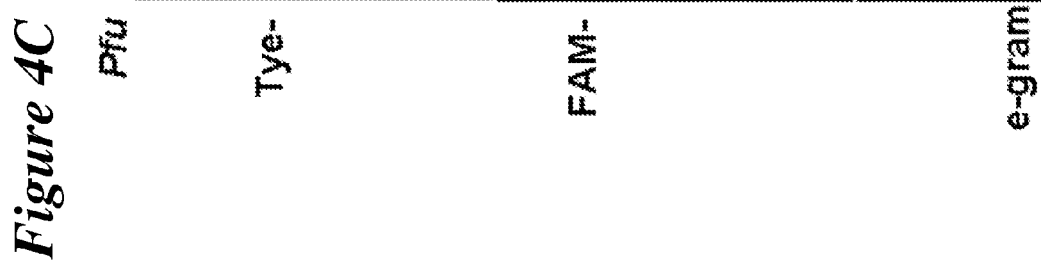
Figure 4D:
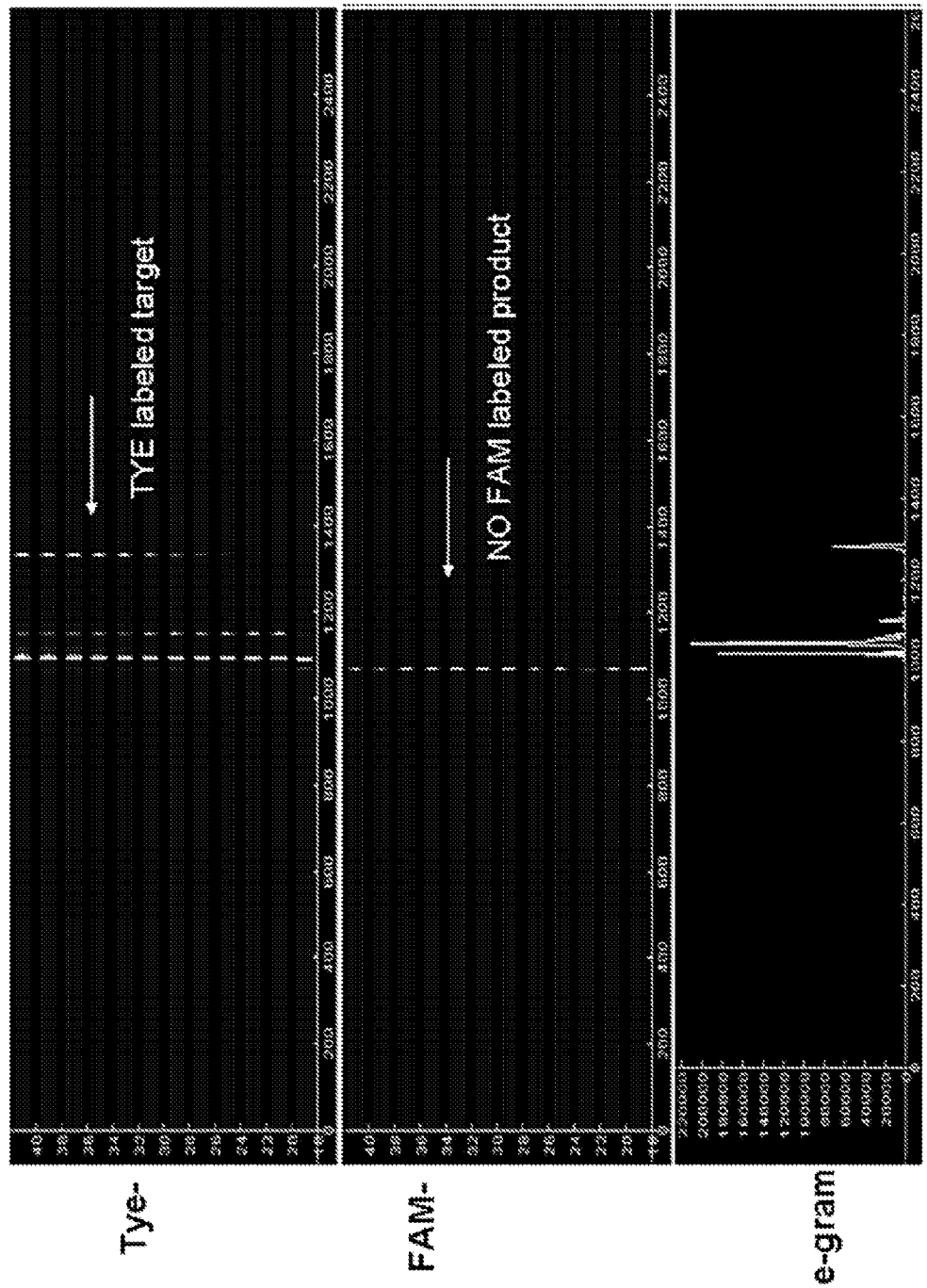

In order to determine the impact of the 5' to 3' exonuclease activity of the polymerases used for generation of the labeled detection molecules having anomalous migration, TAQMAN™-style assays utilizing different polymerase enzymes were performed. As shown in FIGS. 4A-4B, when HOTSTAR TAQ or APTATAQ were used as the polymerases in the amplification reactions, both of which possess 5' to 3' exonuclease activity, an additional FAM-labeled product was detected, in addition to the TYE-labeled amplified target sequence. However, when polymerases lacking 5' to 3' exonuclease activity were utilized, such as Pfu and PyroPage exo-, no additional FAM-labeled product was detected, as shown in FIGS. 4C-4D. Thus, polymerases having 5' to 3' exonuclease activity are required to generate the labeled molecules having anomalous migration properties.

Example 3

Anomalous Migration of Fluorophore Labeled Synthetic Oligonucleotides

Figure 5:
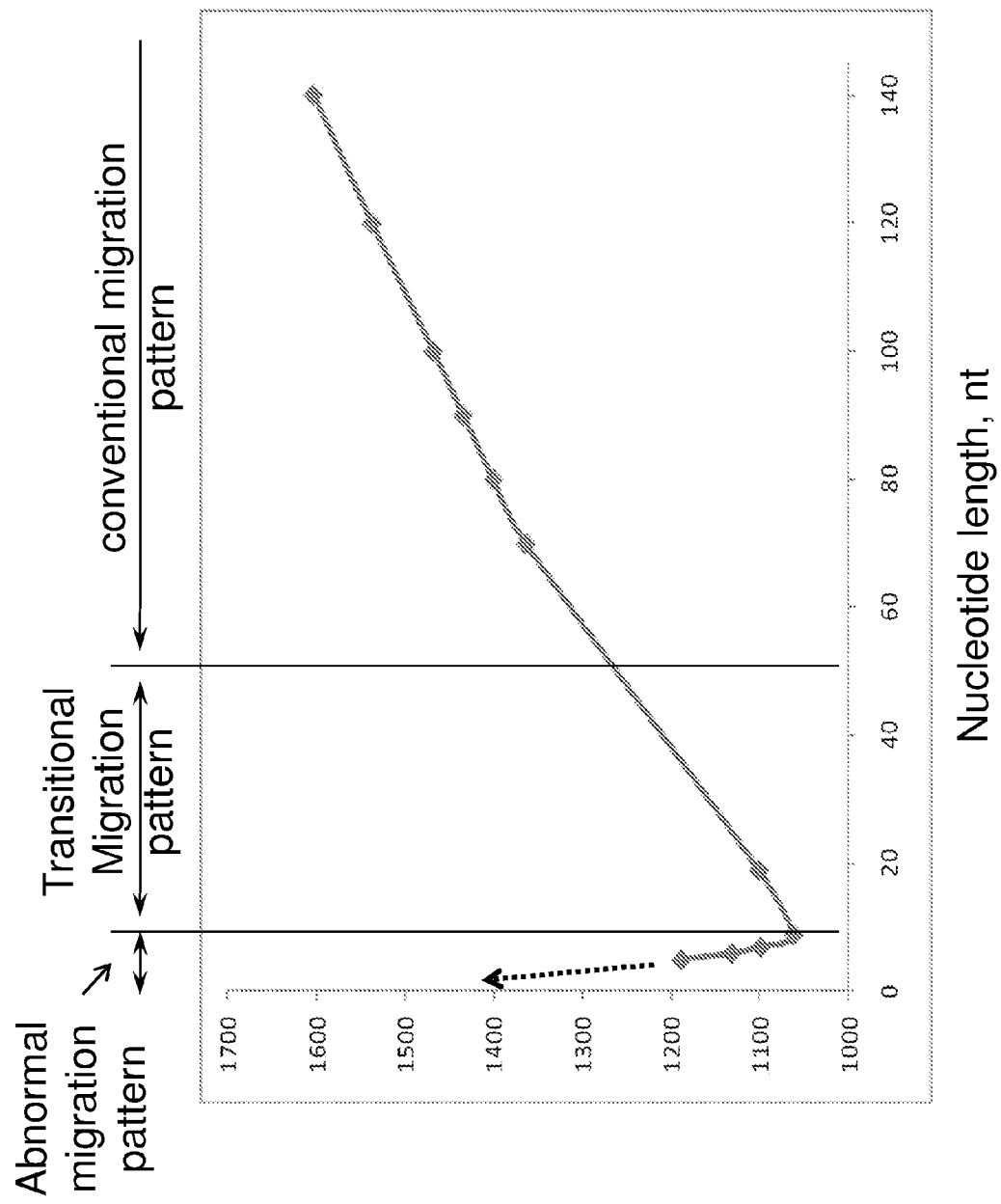
FIG. 5 demonstrates anomalous migration of fluorophore labeled synthetic oligonucleotides. Labeled synthetic nucleotide sequences, comprising 5, 6, 7, or 9 nucleotides, labeled with a FAM fluorophore were prepared and separated by capillary electrophoresis using an ICEPlex system.

In order to identify the nature of the fluorophore-labeled products described in Example 1, labeled synthetic nucleotide sequences, comprising 5, 6, 7, or 9 nucleotides, labeled with a FAM fluorophore were prepared and separated by capillary electrophoresis using an ICEPlex system. As shown in FIG. 5, in contrast to larger nucleotides, the FAM-labeled synthetic nucleotides demonstrated anomalous migration, whereby the FAM-labeled 5 nucleotide sequence migrated slower than the FAM-labeled 6 nucleotide sequence, which migrated slower than the FAM-labeled 7 nucleotide sequence, which migrated slower than the FAM-labeled 9 nucleotide sequence, under the same conditions of separation. Not only did the shortest FAM-labeled nucleotide sequence (5 nucleotides) migrate slower than the largest FAM-labeled nucleotide sequence (9 nucleotides), the anomalous migration of the FAM-labeled 5 nucleotide sequence corresponded to that of a 40 nucleotide sequence.

Example 4

Anomalous Migration of Fluorophore Labeled Non-Target Sequence Products

Figure 6A:
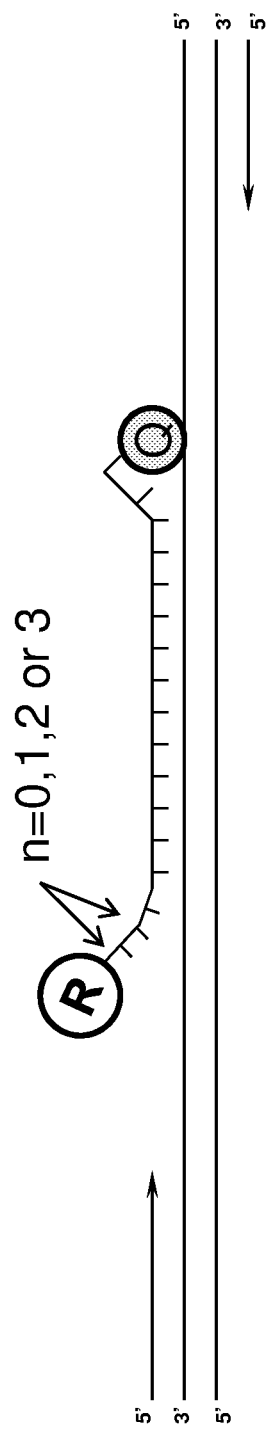
FIGS. 6A-6C demonstrate anomalous migration of fluorophore labeled non-target sequence products. Labeled oligonucleotide probes were designed having non-complementary 5' overhang sequences of varying lengths, as illustrated in FIGS. 6A-6B, for use in TaqMan™-style assays. These experiments were performed with unlabeled or TYE-labeled upstream primers, as illustrated in FIGS. 6A and 6B respectively.
Figure 6B:
Figure 6C:
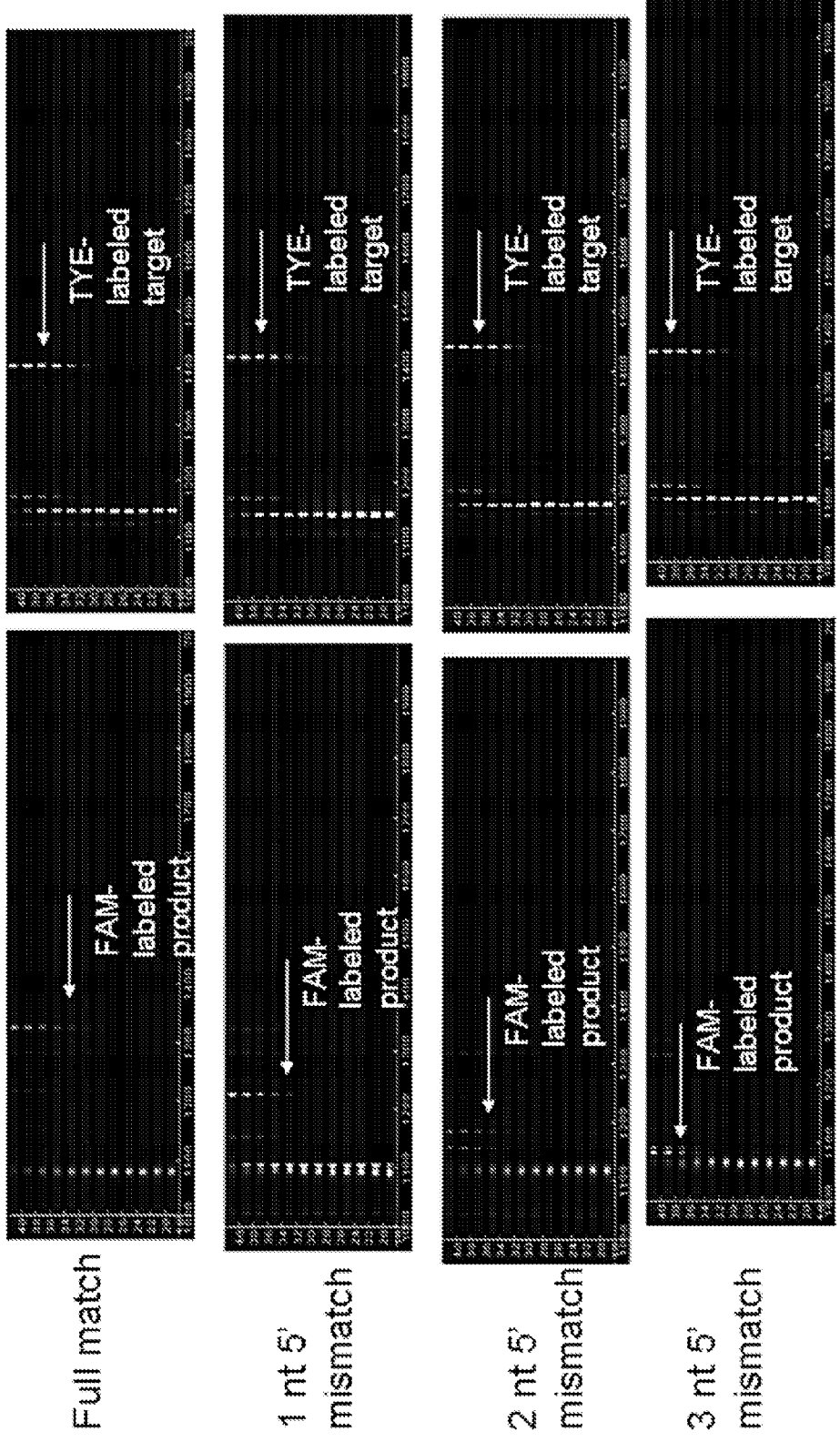

In order to further characterize and elucidate the anomalous migration properties of the labeled nucleotides shown herein, labeled oligonucleotide probes were designed having non-complementary 5' overhang sequences of varying lengths, as illustrated in FIGS. 6A-6B, for use in TAQMAN™-style assays. Accordingly, during the amplification reactions, as the polymerase extends from the 3' end of the primer sequence bound to the target nucleic acid sequence, the 5' to 3' exonuclease activity of the polymerase generates labeled detection molecules having overhang sequences of varying lengths from the downstream labeled oligonucleotide probe annealed to its probe binding site. As shown in FIG. 6C, with increasing lengths of the overhang sequence or mismatch at the 5' end, the faster the labeled detection molecules generated migrated, i.e., anomalous migration. These experiments were performed with unlabeled or TYE-labeled upstream primers. Adjustment of 5' non-complementary overhangs on the labeled oligonucleotide probes can therefore be used to advantage in the quantitative detection of multiplex PCR products.

The invention claimed is:

1. A method for the detection of a target nucleic acid in a sample, the method comprising the steps of:
   a) contacting a nucleic acid sample under hybridizing conditions with an oligonucleotide primer and a FAM-labeled oligonucleotide probe member to create a mixture of hybridized duplexes comprising a primer and a probe member hybridized to the same strand of the same target nucleic acid molecule in said sample, wherein:
      i) said primer hybridizes 5' of said probe member on said target; and
      ii) said probe member hybridizes with said target at the probe's 3' end and comprises a 5' overhang sequence of 0 to n nucleotides that do not hybridize to said target nucleic acid; and
      iii) wherein the FAM-label on said labeled probe is attached to the 5' terminal nucleotide of said probe when the 5' overhang=0 or to one of the n non-hybridizing nucleotides when n>0;
   b) maintaining the mixture of step (a) with a template-dependent nucleic acid polymerase having 5' to 3' nuclease activity, under conditions sufficient to permit the 5' to 3' nuclease activity of the polymerase to cleave the hybridized probe member to release a labeled detection molecule;
   c) separating nucleic acids in said mixture by electrophoresis; and
   d) detecting said FAM-labeled detection molecule in the separated nucleic acids, wherein said FAM-labeled detection molecule indicates the presence of said target molecule, and wherein said FAM-labeled detection molecule is detected in an anomalous migration position for non-hybridizing overhangs of n=0 to 6, with n=1 migrating faster than n=0, n=2 migrating faster than n=1, n=3 migrating faster than n=2, n=4 migrating faster than n=3, n=5 migrating faster than n=4, and n=6 migrating faster than n=5, and where the FAM-labeled detection molecules released from probes with non-hybridizing overhangs greater than n=6 show little change in migration with increasing overhang length, until migration migrate progressively slower with increasing overhang length.

2. The method of claim 1, which permits the detection of a plurality of target nucleic acids in the same nucleic acid sample, wherein step (a) comprises contacting said nucleic acid sample with a primer and probe mixture comprising a different oligonucleotide primer and FAM-labeled oligonucleotide probe member for each of said plurality of target nucleic acids, wherein each of said different FAM-labeled oligonucleotide probe members comprises a different length of non-hybridizing overhang, and wherein the detection of a plurality of the anomalously migrating FAM-labeled detection molecules in step (d) indicates the presence of a plurality of said target molecules.

3. The method of claim 2, wherein said detectably labeled probe members comprise non-hybridizing 5' overhangs of 0 to 6 nucleotides.

4. The method of claim 2, wherein step (a) comprises contacting said nucleic acid sample with a different oligonucleotide primer and detectably labeled oligonucleotide probe member for each of said plurality of target nucleic acids, wherein respective ones of one or more of said detectably labeled oligonucleotide probe members comprise different detectable labels.

5. The method of claim 1, wherein said separating comprises capillary electrophoresis.

6. The method of claim 1, wherein when n=0, the detection molecule has an apparent migration approximately corresponding to that of a 95 base polynucleotide labeled with FAM.

7. The method of claim 1, which permits the detection of a plurality of target nucleic acids in the same nucleic acid sample, wherein step (a) comprises contacting said nucleic acid sample with a different oligonucleotide primer and detectably labeled oligonucleotide probe member for each of said plurality of target nucleic acids, wherein respective ones of one or more of said detectably labeled oligonucleotide probe members comprise different detectable labels, and wherein the detection of labeled detection molecules comprising said different detectable labels indicates the presence of a plurality of said target molecules.

8. The method of claim 7, wherein said different detectable labels comprise fluorescent labels.

9. The method of claim 1, wherein the 3' end of the oligonucleotide primer hybridizes within about 20 nucleotides of the 5' end of the labeled oligonucleotide probe member, thereby having spacing effective to permit the release of labeled fragments in the absence of nucleic acid polymerization.

10. The method of claim 1, wherein the nucleic acid polymerase is a DNA polymerase having a 5' to 3' nuclease activity.

11. The method of claim 10, wherein the DNA polymerase is selected from the group consisting of *Thermus aquaticus* (Taq) polymerase and variants thereof that retain 5' to 3' exonuclease activity; *Thermus thermophiles* (Tth) DNA polymerase; *Bacillus stearothermophilus* DNA polymerase; *Thermus flavus* (Tfl) polymerase; *Thermus brocianus* polymerase; and *E. coli* DNA polymerase.

12. The method of claim 1, wherein said nucleic acid polymerase is a thermostable polymerase.

13. The method of claim 1, wherein the 3' terminal nucleotide of said FAM-labeled oligonucleotide probe cannot be extended by said polymerase.

14. A method for the detection of a target nucleic acid in a sample, the method comprising:
  a) contacting a nucleic acid sample under hybridizing conditions with a pair of oligonucleotide primers and a FAM-labeled oligonucleotide probe to create a mixture of hybridized duplexes of said pair of oligonucleotide primers and said FAM-labeled probe annealed to a target nucleic acid present in said sample,
    wherein the pair of oligonucleotide primers comprises a first oligonucleotide primer that hybridizes to the antisense of a 5' region of the target nucleic acid and a second oligonucleotide primer that hybridizes to a 3' region of the target nucleic acid,
    wherein said first oligonucleotide primer and said FAM-abeled oligonucleotide probe hybridize to the same strand of said target nucleic acid,
    wherein said 5' and 3' regions of said target sequence flank a region of said target sequence to which said FAM-labeled oligonucleotide probe hybridizes, and
    wherein said FAM-labeled oligonucleotide probe comprises a 5' overhang sequence of 0 to n nucleotides that does not hybridize to said target nucleic acid, and wherein the FAM label on said labeled probe is attached to the 5' terminal nucleotide of said probe when 5' overhang=0 or to one of the n non-hybridizing nucleotides when n>0;
  b) PCR (polymerase chain reaction) amplifying target nucleic acid molecules present in said sample by a plurality of cycles of:
    i) extending annealed oligonucleotide primers using a thermostable nucleic acid polymerase having 5' to 3' exonuclease activity, under conditions sufficient to permit primer extension of annealed oligonucleotide primers and to permit the 5' to 3' nuclease activity to cleave annealed oligonucleotide probe to thereby release a labeled detection molecule;
    ii) heating to separate nucleic acid strands generated in step (i); and
    iii) maintaining under temperature conditions that permit annealing of oligonucleotide primer pairs and labeled oligonucleotide probes to target nucleic acids present in said sample;
  c) separating nucleic acids generated in step (b); and
  d) detecting a released FAM-labeled detection molecule in the separated nucleic acids to thereby detect the presence and/or amount of said target nucleic acid present in said sample, wherein FAM-labeled detection molecule is detected in an anomalous migration position for a non-hybridizing overhang of n=0 to 6, with n=1 migrating faster than n=0, n=2 migrating faster than n=1, n=3 migrating faster than n=2, n=4 migrating faster than n=3, n=5 migrating faster than n=4, and n=6 migrating faster than n=5, and where the FAM-labeled detection molecules released from probes with non-hybridizing overhangs greater than n=6 show little change in migration with increasing overhang length, until migration migrate progressively slower with increasing overhang length.

15. The method of claim 14, wherein said separating comprises capillary electrophoresis.

16. The method of claim 14, wherein said FAM-labeled probe member comprises a non-hybridizing 5' overhang of 0 to 6 nucleotides.

17. The method of claim 14, wherein when n=0, the detection molecule has an apparent migration corresponding to that of an approximately 95 base polynucleotide labeled with FAM.

18. The method of claim 14, wherein the 3' terminal nucleotide of said FAM-labeled oligonucleotide probe cannot be extended by said polymerase.

19. A method for the multiplex detection of target nucleic acids in a sample, the method comprising:
  a) contacting a nucleic acid sample under hybridizing conditions with a pair of oligonucleotide primers and a fluorescently labeled oligonucleotide probe for each member of a plurality of different nucleic acid targets to be detected in said sample, to create a mixture of hybridized duplexes of said pair of oligonucleotide primers and said fluorescently labeled probe specific for each said target nucleic acid member present in said sample, wherein:
    i) for each nucleic acid target, the pair of oligonucleotide primers comprises a first oligonucleotide primer that hybridizes to the antisense of a 5' region of the target nucleic acid and a second oligonucleotide primer that hybridizes to a 3' region of the target nucleic acid;
    ii) for each nucleic acid target, said 5' and 3' regions of said target sequence flank a region of said target sequence which is complementary to said fluorescently labeled oligonucleotide probe,
    iii) said first oligonucleotide primer and said fluorescently labeled oligonucleotide probe for each nucleic acid target hybridize to the same strand of said target nucleic acid, and
    iv) at least one fluorescently labeled probe is FAM-labeled, and wherein when the fluorescently labeled probe is FAM-labeled, said probe comprises a 5' overhang sequence of 0 to n nucleotides that do not hybridize to the target nucleic acid, where the FAM label on the labeled probe is attached to the 5' terminal nucleotide of the probe when the overhang=0 or to one of the n non-hybridizing nucleotides when n>0, and wherein each different FAM-labeled probe has a different length of 5' overhang; and
    v) the length n of 5' overhang sequence and/or the identity of the label differs for each different target sequence to be detected;
  b) PCR amplifying target nucleic acid molecules present in said sample by a plurality of cycles of:
    i) extending annealed oligonucleotide primers using a nucleic acid polymerase having 5' to 3' exonuclease activity, under conditions sufficient to permit primer extension of annealed oligonucleotide primers and to permit the 5' to 3' nuclease activity to cleave annealed oligonucleotide probes and thereby release a fluorescently labeled detection molecule specific for each of the plurality of target nucleic acids present in said sample;
    ii) heating to separate nucleic acid strands generated in step (i); and
    iii) annealing oligonucleotide primer pairs and fluorescently labeled oligonucleotide probes to target nucleic acids present in said sample;
  c) separating nucleic acids generated in step (b) such that fluorescently labeled detection molecules specific for each of said target nucleic acids present in said sample can be identified; and
  d) detecting each of said fluorescently labeled detection molecules released, whereby the presence and/or amount of each of said plurality of target nucleic acids present in said sample is indicated, wherein FAM-labeled detection molecules are detected in an anomalous migration position for a non-hybridizing overhang of n=0 to 6, with n=1 migrating faster than n=0, n=2 migrating faster than n=1, n=3 migrating faster than n=2, n=4 migrating faster than n=3, n=5 migrating faster than n=4, and n=6 migrating faster than n=5, and where the FAM-labeled detection molecules released from probes with non-hybridizing overhangs greater than n=6 show little change in migration with increasing overhang length, until migration migrate progressively slower with increasing overhang length.

20. The method of claim 19, wherein said separating comprises capillary electrophoresis.

21. The method of claim 19, wherein when n=0, the FAM-labeled detection molecule has an apparent migration corresponding to that of an approximately 95 base polynucleotide labeled with FAM.

22. The method of claim 19, wherein the 3' terminal nucleotide of each said fluorescently-labeled oligonucleotide probe cannot be extended by said polymerase.

23. The method of claim 19, wherein said fluorescently labeled detection molecules specific for each of said target molecules present in said sample differ from each other in the separation characteristics of the released detection molecule, wherein said separation characteristics comprise, mass, length, charge, or a combination thereof.

* * * * *